US012807734B2

(12) United States Patent
Shelef

(10) Patent No.: US 12,807,734 B2
(45) Date of Patent: Nov. 24, 2026

(54) IGG EPITOPE PEPTIDES THAT BIND RHEUMATOID FACTOR AND METHODS OF USE THEREOF

(71) Applicant: Wisconsin Alumni Research Foundation, Madison, WI (US)

(72) Inventor: Miriam Shelef, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 874 days.

(21) Appl. No.: 18/079,188

(22) Filed: Dec. 12, 2022

(65) Prior Publication Data

US 2023/0212316 A1 Jul. 6, 2023

Related U.S. Application Data

(60) Provisional application No. 63/289,749, filed on Dec. 15, 2021.

(51) Int. Cl.

| | |
|---|---|
| ***C07K 16/42*** | (2006.01) |
| ***A61K 45/06*** | (2006.01) |
| ***A61P 19/02*** | (2006.01) |
| ***A61P 31/14*** | (2006.01) |
| ***G01N 33/564*** | (2006.01) |

(52) U.S. Cl.

CPC .............. *C07K 16/42* (2013.01); *A61K 45/06* (2013.01); *A61P 19/02* (2018.01); *A61P 31/14* (2018.01); *G01N 33/564* (2013.01)

(58) Field of Classification Search

CPC ................................ C07K 16/42; A61P 19/02
See application file for complete search history.

(56) References Cited

U.S. PATENT DOCUMENTS

| | | | | |
|---|---|---|---|---|
| 8,436,147 B2 * | 5/2013 | Dennis | C07K 16/3069 530/391.1 |
| 9,359,438 B2 * | 6/2016 | Sexton | A61P 37/06 530/391.1 |

OTHER PUBLICATIONS

Mergaert, A. et al.; "Rheumatoid Factor and Anti-Modified Protein Antibody Reactivities Converge on IgG Epitopes"; Arthritis & Rheumatology, vol. 74, Issue No. 6; 2022; pp. 984-991; DOI: 10.1002/art.42064.

Zheng, Z. et al.; "Disordered Antigens and Epitope Overlap Between Anti-CitrullinatedProtein Antibodies and Rheumatoid Factor in Rheumatoid Arthritis"; Arthritis & Rheumatology, vol. 72, Issue No. 2; 2020; pp. 262-272; DOI: 10.1002/art.41074.

Amara, K. et al.; "A Refined Protocol for Identifying Citrulline-specific Monoclonal Antibodies from Single Human B Cells from Rheumatoid Arthritis Patient Material"; Bio Protocol, vol. 9, Issue No. 17, e3347; 2019; 39 pages.

Artandi, S. et al.; "Monoclonal IgM rheumatoid factors bind IgG at a discontinuous epitope comprised of amino acid loops from heavy-chain constant-region domains 2 and 3"; PNAS USA, vol. 89, Issue No. 1; 1992; pp. 94-98.

Borretzen, M. et al.; "Control of autoantibody affinity by selection against amino acid replacements in the complementarity-determining regions"; PNAS USA, vol. 91, Issue No. 26; 1994; pp. 12917-12921.

Falkenburg, W., et al.; "Anti-Hinge Antibodies Recognize IgG Subclass- and Protease-Restricted Neoepitopes"; Journal of Immunology, vol. 198, Issue No. 1; 2017; pp. 82-93.

Gronwall, C. et al.; "A Comprehensive Evaluation of the Relationship Between Different IgG and IgA Anti-Modified Protein Autoantibodies in Rheumatoid Arthritis"; Frontiers in Immunology, vol. 12, Article No. 627986; 2021; 22 pages.

Hedstrom, A. et al.; "Complex Relationships of Smoking, HLADRB1 Genes, and Serologic Profiles in Patients With Early Rheumatoid Arthritis: Update From a Swedish Population-Based Case-Control Study"; Arthritis & Rheumatology, vol. 71, Issue No. 9; 2019; pp. 1504-1511.

Holmes, C., et al.; "Reduced IgG titers against pertussis in rheumatoid arthritis: Evidence for a citrulline-biased immune response and medication effects"; PLoS One, vol. 14, Issue No. 5, e0217221; 2019; 16 pages; https://doi.org/10.1371/journal.pone.0217221.

Kelmenson, L. et al.; "Timing of Elevations of Autoantibody Isotypes Prior to Diagnosis of Rheumatoid Arthritis"; Arthritis Rheumatology, vol. 72, Issue No. 2; 2020; pp. 251-261.

Lloyd, K. et al.; "Differential ACPA Binding to Nuclear Antigens Reveals a PAD-Independent Pathway and a Distinct Subset of Acetylation Cross-Reactive Autoantibodies in Rheumatoid Arthritis"; Frontiers in Immunology, vol. 9, Issue No. 3033; 2018; 22 pages; doi: 10.3389/fimmu.2018.03033.

Maibom-Thomsen, S. et al.; "Immunoglobulin G structure and rheumatoid factor epitopes"; PLoS One, vol. 14, Issue No. 6, e0217624; 2019; 28 pages; doi: https://doi.org/10.1371/journal.pone.0217624.

Mikuls, T. et al.; "Autoantibodies to Malondialdehyde-Acetaldehyde Are Detected Prior to Rheumatoid Arthritis Diagnosis and After Other Disease Specific Autoantibodies"; Arthritis & Rheumatology, vol. 72, Issue 12; 2020; pp. 2025-2029.

Morell, A. et al.; "Correlations between the concentrations of the four sub-classes of IgG and Gm Allotypes in normal human sera"; Journal of Immunology, vol. 108, Issue No. 1; 1972; pp. 195-206.

Newkirk, M. et al.; "Chronic smoke exposure induces rheumatoid factor and anti-heat shock protein 70 autoantibodies in susceptible mice and humans with lung disease"; European Journal of Immunology, vol. 42, Issue No. 4; 2012; pp. 1051-1061.

(Continued)

*Primary Examiner* — Sue X Liu

(74) *Attorney, Agent, or Firm* — Karen Lecuyer; Dewitt LLP

(57) ABSTRACT

Described herein are IgG epitope peptides that bind rheumatoid factors in rheumatoid arthritis (RA) and COVID-19. The IgG epitope peptides may be conjugated to a ligand, a detectable label, or a combination thereof. Also, the IgG epitope peptides are particularly useful in assays to detect antibodies in blood samples from subjects with RA risk factors, for example. The COVID-19 IgG epitope peptides are particularly useful in screening convalescent plasma.

13 Claims, 13 Drawing Sheets

Specification includes a Sequence Listing.

(56) References Cited

OTHER PUBLICATIONS

Petri, M. et al. Derivation and validation of the Systemic Lupus International Collaborating Clinics classification criteria for systemic lupus erythematosus. Arthritis and Rheumatism, vol. 64, Issue No. 8; 2012; pp. 2677-2686.
Rebernick, R. et al.; "DNA Area and NETosis Analysis (DANA): a High-Throughput Method to Quantify Neutrophil Extracellular Traps in Fluorescent Microscope Images"; Biology Procedures Online, vol. 20, Article No. 7; 2018; 9 pages; doi: https://doi.org/10.1186/s12575-018-0072-y.
Sahlstrom, P. et al.; "Different Hierarchies of Anti-Modified Protein Autoantibody Reactivities in Rheumatoid Arthritis"; Arthritis & Rheumatology, vol. 72, Issue No. 10; 2020; pp. 1643-1657.
Schellekens, G. et al.; "Citrulline is an essential constituent of antigenic determinants recognized by rheumatoid arthritis-specific autoantibodies"; Journal of Clinical Investigation, vol. 101, Issue No. 1; 1998; pp. 273-281.
Shi, J. et al.; "Autoantibodies recognizing carbamylated proteins are present in sera of patients with rheumatoid arthritis and predict joint damage"; PNAS USA, vol. 108, Issue No. 42; 2011; pp. 17372-7.
Shiboski, C. et al.; "2016 American College of Rheumatology/European League Against Rheumatism Classification Criteria for Primary Sjogren's Syndrome: A Consensus and Data-Driven Methodology Involving Three International Patient Cohorts"; Arthritis & Rheumatology, vol. 69, Issue No. 1; 2017; pp. 35-45.
Steen, J. et al.; "Recognition of Amino Acid Motifs, Rather Than Specific Proteins, by Human Plasma Cell-Derived Monoclonal Antibodies to Posttranslationally Modified Proteins in Rheumatoid Arthritis"; Arthritis & Rheumatology, vol. 71, Issue No. 2; 2019; pp. 196-209.
Terness, P. et al. "The natural human IgG anti-F(ab')2 antibody recognizes a conformational IgG1 hinge epitope"; Journal of Immunology, vol. 154, Issue No. 12; 1995; pp. 6446-6452.
Titcombe, P. et al.; "Pathogenic Citrulline-Multispecific B Cell Receptor Clades in Rheumatoid Arthritis"; Arthritis & Rheumatology, vol. 70, Issue No. 12; 2018; pp. 1933-1945.
Zheng, Z. et al.; "MixTwice: large-scale hypothesis testing for peptide arrays by variance mixing"; Bioinformatics, vol. 37, Issue No. 17; 2021; pp. 2637-2643.

* cited by examiner

IGG EPITOPE PEPTIDES THAT BIND RHEUMATOID FACTOR AND METHODS OF USE THEREOF

CROSS-REFERENCE TO RELATED APPLICATIONS

This application claims priority to U.S. Provisional Application 63/289,749 filed on Dec. 15, 2021, which is incorporated herein by reference in its entirety.

STATEMENT REGARDING FEDERALLY SPONSORED RESEARCH & DEVELOPMENT

This invention was made with government support under W81XWH-18-1-0717 awarded by the ARMY/MRMC. The government has certain rights in the invention.

SEQUENCE LISTING

The Instant Application contains a Sequence Listing which has been submitted electronically in XML format and is hereby incorporated by reference in its entirety. Said XML copy, created on Jun. 16, 2026, is named "SEQ_LIST-107668366-P230082WO01" and is 26,447 bytes in size. The Sequence Listing does not go beyond the disclosure in the application as filed.

FIELD OF THE DISCLOSURE

The present disclosure is related to IgG peptides that bind rheumatoid factors (RFs) involved in rheumatoid arthritis (RA) and/or COVID-19.

BACKGROUND

Two main types of autoantibodies with high diagnostic value and possible pathogenic roles exist in rheumatoid arthritis (RA): rheumatoid factor (RF) and anti-citrullinated protein antibodies (ACPAs). RFs, antibodies of any isotype that bind the Fc portion of IgG, are common in RA, but are also found less frequently in systemic lupus erythematosus, anti-SSA+Sjogren's disease, ankylosing spondylitis, some infections, hematologic malignancy, and smokers. RFs commonly bind to two conformational epitopes after antigen binding, enzymatic degradation, or other change to the IgG molecule: one in the hinge region and one that includes parts of the CH2 and CH3 regions. In RA, additional epitopes are bound, affinity maturation occurs, and IgG-RF and IgA-RF are common, evidence of T cell help. However, why tolerance against IgG is lost in T cells in RA is unknown.

In addition to RFs, approximately 75% of RA patients develop ACPAs, autoantibodies against proteins containing arginines that were post-translationally modified to citrullines. Unlike RFs, ACPAs are highly specific for RA and associated with shared epitope-containing HLA alleles, which may contribute to their development. Autoantibodies have also been identified in RA that bind to epitopes in which lysines have been converted to homocitrullines, i.e., homocitrullinated (carbamylated) antigens. Moreover, individual ACPAs are often "anti-modified protein antibodies (AMPAs)" given their frequent reactivity to homocitrullinated and acetylated epitopes in addition to their multireactivity to many citrullinated targets. Why AMPAs and RFs typically coexist in RA is a long-standing mystery.

Recently, IgG in RA sera was shown to bind to citrulline-containing linear peptides present in the constant region of the IgG heavy chain, raising the possibility that IgG could be a shared antigen for RFs and AMPAs. However, although RF is defined by binding to IgG, it is unknown if AMPAs could recognize modified IgG epitopes. Moreover, the use of modern technology to discover new IgG epitopes in a few RA patients raised the possibility of additional unexplored IgG epitopes in RA and other rheumatic diseases with RF.

Described herein are novel IgG epitopes identified by evaluating the repertoire of IgG heavy chain derived linear peptides bound by antibodies in rheumatic diseases including RA and by monoclonal AMPAs (mAMPAs). Also described herein are novel IgG epitopes identified using similar methods in subjects who recently recovered from COVID-19. Finally, use of these epitopes to identify individuals at risk for developing RA is described.

BRIEF SUMMARY

In an aspect, a peptide comprises any of SEQ ID NOs. 3, 6, 11, 14, 19, 24, 25, or 26, wherein each X1 is K or J, and each X2 is R or B, or a variant with 1-6 variant amino acids at positions other than those including X1, X2, K, J, R, and B, wherein the variant peptide detects bound IgA, IgM, IgG1-4, IgE antibodies, or a combination thereof, in an ELISA assay (See Table 1). Also included are devices and substrates comprising the peptides.

In another aspect, a method of testing a body fluid or tissue sample from a subject comprises contacting the blood sample with a peptide as described above and detecting complexes of the peptide and antibodies in the body fluid or tissue sample.

In another aspect, a method of detecting rheumatoid factor in a blood sample from a subject comprises contacting the blood sample with a peptide as described above and detecting complexes of the peptide and antibodies in the body fluid or tissue sample.

In another aspect, a method of treating a subject comprises contacting a body fluid or tissue sample from the subject with a peptide as described above, detecting complexes of the peptide and antibodies in the body fluid or tissue sample, and, upon detection of complexes, administering to the subject a pre-rheumatoid arthritis treatment.

In a further aspect, a peptide comprises

```
                                 (SEQ ID NO: 25)
DKTHTCPPCPAPELLG,

                                 (SEQ ID NO: 27)
KDTLMISRTPEVTCVV,

                                 (SEQ ID NO: 28)
RDELTKNQVSLTCLVK,
or

                                 (SEQ ID NO: 29)
LTVDKSRWQQGNVFSC,
or
```

or a variant with 1-6 variant amino acids, wherein the variant peptide detects bound IgA, IgM, IgG1-4, IgE antibodies, or a combination thereof, in an ELISA assay. Also included are devices and substrates comprising the peptides.

In a further aspect, method of testing a bodily fluid or tissue sample from a subject comprises contacting the blood sample with a peptide of the preceding paragraph and detecting complexes of the peptide and antibodies in the bodily fluid or tissue sample.

In a yet further aspect, a method of screening convalescent plasma from a subject recovered from COVID-19 comprises contacting the convalescent plasma sample from the subject with a peptide of the preceding two paragraphs and detecting complexes of the peptide and antibodies in the convalescent plasma sample, wherein convalescent plasma containing detectable complexes is selected.

In another aspect, a substrate or device comprises peptides of SEQ ID NOs. 1, 2, 4, 5, 7-10, 12, 13, 15-18, 20-23, 25 and/or 26-29 or a variant with 1-6 variant amino acids at positions wherein the variant peptide detects bound IgA, IgM, IgG1-4, IgE antibodies, or a combination thereof, in an ELISA assay. Such an assay could be used to evaluate RFs in a biological sample from any individual to help diagnose and differentiate between pre-clinical RA, RA, Sjogren's disease, lupus, smokers, and recent infection like COVID-19.

BRIEF DESCRIPTION OF THE DRAWINGS

FIG. 7A. Rheumatoid factors (RFs) were quantified in a traditional manner by measuring total Ig binding to the Fc portion of IgG by ELISA in the sera of COVID-19 convalescent subjects collected 5 weeks post-symptom resolution and COVID-19 naïve subjects collected prior to 2019. RF binding was increased in some convalescent subjects.

Figure 1:
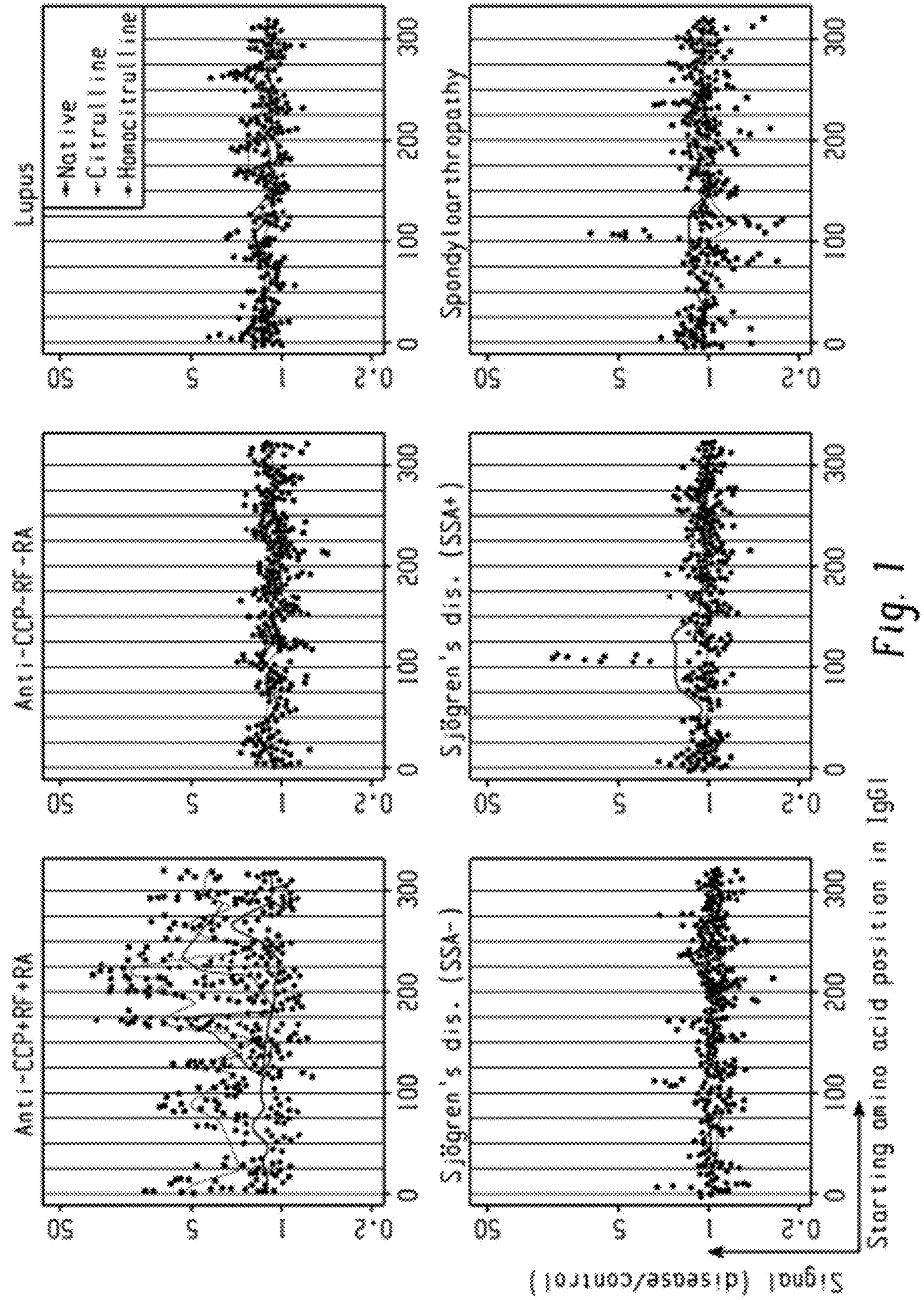
FIG. 1 shows serum IgG binding to IgG1-derived peptides in rheumatic diseases. Serum IgG binding was quantified for every 12 amino acid linear peptide derived from the constant region of the heavy chain of human IgG1 using a high density peptide array and sera from patients diagnosed with RA (anti-CCP+RF+ and anti-CCP-RF−), lupus, Sjögren's disease (anti-SSA+ and anti-SSA−), spondyloarthropathy, and age- and gender-matched control subjects. IgG binding signal for each disease group divided by control binding signal is graphed for each peptide according to its starting position in the constant region of the heavy chain of IgG1 (n=8 except n=16 lupus).

The above-described and other features will be appreciated and understood by those skilled in the art from the following detailed description, drawings, and appended claims.

DETAILED DESCRIPTION

Rheumatoid factors (RFs) are antibodies that bind to the constant (Fc) region of IgG. They are extremely common in rheumatoid arthritis, an incurable autoimmune arthritis that affects approximately 1% of the population, but also rise in 10-20% of individuals with infection or other inflammatory problems. In infection, RFs are thought to bind to pathogen-antibody immune complexes, or possibly pathogens directly in a cross-reactive manner, to enhance pathogen neutralization and clearance.

Rheumatoid arthritis (RA) is the most common autoimmune joint disease. In RA, joint tissues are affected by chronic synovial inflammation, synovial hyperplasia and destruction of joint cartilage and bone. Despite the development of conventional disease modifying anti-rheumatic drugs (DMARDs) and biologic drugs, remission rarely occurs, and RA progresses to joint dysfunction and disability. The therapeutic window of opportunity for initiation of therapeutic intervention to prevent joint destruction is very early in the course of RA. Methods that can lead to diagnosis of pre-clinical rheumatoid arthritis, i.e., the time period when immunologic derangements like autoantibodies develop prior to clinical arthritis, are of critical importance.

In rheumatoid arthritis, RFs are thought to be pathologic through a similar mechanism that they are helpful in infection: by binding to autoantibody-autoantigen immune complexes to amplify the immune response. Interestingly, the other common antibody type in rheumatoid arthritis, anti-citrullinated protein antibodies, rises approximately 17 years prior to rheumatoid arthritis. RFs often rise 7 years or less prior to diagnosis, at the same time as inflammatory cytokines, suggesting that they may be part of the mechanism that drives imminent clinical disease. Although RFs have been thought to have relatively uniform reactivity across conditions, described herein are epitopes of IgG bound uniquely in rheumatoid arthritis, Sjögren's disease, and COVID-19.

IgG Epitopes in Ra and Sjögren'S Disease and Methods of Use

The IgG epitopes of IgG bound in rheumatoid arthritis and Sjogren's disease include the sequences in Table 1. As used herein, B represents citrulline and J represents homocitrulline.

TABLE 1

| SEQ ID NO: | Sequence |
|---|---|
| 1 | LAPSS**K**STSGGTAALGC |
| 2 | LAPSS**J**STSGGTAALGC |
| 3 | LAPSS**X1**STSGGTAALGC, wherein X1 is K or J, or written alternatively LAPSS**X**STSGGTAALGC, wherein X at position 6 is K or homocitrulline |
| 4 | TYICNVNH**K**PSNT**K**VD**KK**VEP**K**SC |
| 5 | TYICNVNH**J**PSNT**J**VD**JJ**VEP**J**SC |
| 6 | TYICNVNH**X1**PSNT**X1**VD**X1X1**VEP**X1**SC, wherein X1 is K or J, or written alternatively TYICNVNH**X**PSNT**X**VD**XX**VEP**X**SC, where X at positions 9, 14, 17, 18, and 22 are K or homocitrulline |
| 7 | VHNA**K**T**K**P**R**EEQYNSTY**R**VVSV |
| 8 | VHNA**K**T**K**P**B**EEQYNSTY**B**VVSV |
| 9 | VHNA**J**T**J**P**R**EEQYNSTY**R**VVSV |
| 10 | VHNA**J**T**J**P**B**EEQYNSTY**B**VVSV |
| 11 | VHNA**X1**TX1P**X2**EEQYNSTY**X2**VVSV, wherein X1 is K or J, and X2 is R or B, or written alternatively VHNA**X**T**X**P**X**EEQYNSTY**X**VVSV, wherein X at positions 5 and 7 is K or homocitrulline, and X at positions 9 and 18 is R or citrulline |
| 12 | Y**K**C**K**VSN**K**ALPAP |
| 13 | Y**J**C**J**VSN**J**ALPAP |
| 14 | Y**X1**C**X1**VSN**X1**ALPAP, wherein X1 is K or J, or written alternatively Y**X**C**X**VSN**X**ALPAP, wherein X at positions 2, 4, and 8 is K or homocitrulline |
| 15 | IS**K**A**K**GQP**R**EPQVYTLPPS**R**DEL |
| 16 | IS**J**A**J**GQP**R**EPQVYTLPPS**R**DEL |
| 17 | IS**K**A**K**GQP**B**EPQVYTLPPS**B**DEL |
| 18 | IS**J**A**J**GQP**B**EPQVYTLPPS**B**DEL |
| 19 | IS**X1**A**X1**GQP**X2**EPQVYTLPPS**X2**DEL, wherein X1 is K or J, and X2 is R or B, or written alternatively IS**X**A**X**GQP**X**EPQVYTLPPS**X2**DEL, wherein X at positions 3 and 5 is K or homocitruline, and X at positions 9 and 20 is R or citrulline |
| 20 | LYS**K**LTVD**K**S**R**WQQGNVFS |
| 21 | LYS**K**LTVD**K**S**B**WQQGNVFS |
| 22 | LYS**J**LTVD**J**S**R**WQQGNVFS |
| 23 | LYS**J**LTVD**J**SBWQQGNVFS |
| 24 | LYS**X1**LTVD**X1**S**X2**WQQGNVFS, wherein X1 is K or J, and X2 is R or B; or written alternatively LYS**X**LTVD**X**S**X**WQQGNVFS, wherein X at position 4 is K or J, X at position 9 is K or J, and X at position 11 is R or B |

TABLE 1-continued

| SEQ ID NO: | Sequence |
|---|---|
| 25 | DKTHTCPPCPAPELLG |
| 26 | CPPCPAPELLGGPSV |

In Table 1, each instance of X1 is independently K or J. In an aspect, all instances of X1 are K or all instances of X1 are J in an individual peptide. Also, in Table 1, each instance of X2 is independently R or B. In an aspect, all instances of X1 are R or all instances of X2 are B in an individual peptide.

In Table 1, IN SEQ ID NO: 24, X at positions 4 and 9 is independently K or J. In an aspect, X at positions 4 and 9 are both K or X at positions 4 and 9 are both J in an individual peptide. Also, in Table 1, X a position 11 is R or B. In an aspect, all instances of X at position 11 are R or all instances of X at position 11 are B in an individual peptide.

Also included herein are peptides that are homologous to the peptides of Table 1, such as peptides with 1-6, 1-5, 1-4, 1-3, or 1-2 variant amino acids at positions other than those including X1, X2, K, J, R, and B, so long as the peptides can detect bound IgA, IgM, IgG1-4, and/or IgE antibodies in a standard ELISA.

In an aspect, the IgG epitope peptides do not comprise a full-length IgG constant region, for example, the epitope peptide comprises 10 to 100 or more contiguous amino acids of an IgG constant region. In a further aspect, the IgG epitope peptides are conjugated to a ligand, a detectable label, or a combination thereof. Ligands and detectable labels are described below.

Also included herein are supports and devices comprising the IgG epitope peptides. Supports and devices are described below.

Currently, there are no diagnostic tests that differentiate between RFs in rheumatoid arthritis and other conditions and no test that identifies which individuals are on the cusp of developing rheumatoid arthritis for consideration of preventative immunosuppression. The peptides from Table 1 can be used in these methods.

In an aspect, a method of testing a body fluid or tissue sample from a subject comprises contacting the blood sample with a peptide of any of SEQ ID NOs. 1-26, and detecting complexes of the peptide and antibodies in the body fluid or tissue sample.

In another aspect, a method of detecting rheumatoid factor in a body fluid or tissue sample from a subject comprises contacting the blood sample with a peptide of any of SEQ ID NOs. 1-26, and detecting complexes of the peptide and antibodies in the body fluid or tissue sample.

Exemplary samples include blood samples such as serum or plasma samples, synovial fluid or tissue, bronchiolar lavage fluid, or lung tissue, for example.

In an aspect, the peptide is immobilized on a solid support.

Detecting can comprise binding to a peptide array, flow cytometry, performing an ELISA, multiplex assay, immunofluorescence assay, or a lateral flow immunoassay.

Immunoassay methods can include receiving or obtaining a sample; contacting (e.g., incubating or reacting) the sample to be assayed with a peptide of Table 1, under conditions effective for the formation of a specific peptide-RF complex (e.g., for specific binding of the peptide to RF); and assaying the contacted (reacted) sample for the presence of an antibody-RF reaction (e.g., determining the amount of an antibody-peptide complex). In an ELISA assay, a positive response may be defined as a value 2 or 3 standard deviations greater than the mean value of a group of healthy controls. In the assay, the peptide may be labeled (e.g., metallic nanoparticle, fluorescent label, enzyme (e.g., horseradish peroxidase or alkaline phosphatase)) or a labeled substance, such as a binding partner or a labeled antibody which specifically recognizes RF may be added.

The protocols for immunoassays using antigens for detection of specific antibodies are well known in art. For example, a conventional sandwich assay can be used, or a conventional competitive assay format can be used.

In an aspect, a method of treating a subject not diagnosed with rheumatoid arthritis comprises contacting a body fluid or tissue sample from the subject with a peptide of any of SEQ ID NOs. 1-26, detecting complexes of the peptide and antibodies in the body fluid or tissue sample, and, upon detection of complexes, administering to the subject a preventative treatment for rheumatoid arthritis. Such a subject may be referred to as having pre-clinical rheumatoid arthritis.

Exemplary subjects in need of testing for detecting complexes of the peptide and antibodies such as rheumatoid factor and/or AMPAs include subjects at risk of developing rheumatoid arthritis such as subjects having a parent or sibling with rheumatoid arthritis, subjects with arthralgia and not arthritis, subjects testing positive for anti-citrullinated peptide (CCP) antibodies, subjects having rheumatoid arthritis risk variants in the human leukocyte antigen (HLA) system or other genetic risk factors, and subjects having a previous bacterial or viral infection or are colonized with certain pathogens such as Epstein-Barr virus, cytomegalovirus, *P. gingivalis, A. actinomycetemcomitans*, or *Prevotella* species, subjects who smoke, subjects who are obese, and men who have aged more than 50 years or women who have aged more than 30 years.

Exemplary pre-clinical rheumatoid arthritis treatments could include administration of glucocorticoids, vitamins such as vitamin D, supplements such as omega-3 fatty acids, disease-modifying anti-rheumatic drugs (DMARDs) such as azathioprine, cyclophosphamide, cyclosporin, hydroxychloroquine, leflunomide, methotrexate, mycophenolate mofetil, sulfasalazine, infliximab, adalimumab, etanercept, rituximab, abatacept, tocilizumab; Janus kinase (JAK) inhibitors such as baricitinib, tofacitinib, upadacitinib; and combinations thereof.

Any of the foregoing methods may further comprise detecting anti-modified protein antibodies such as anti-citrullinated protein antibodies (ACPAs), anti-homocitrullinated protein antibodies, or anti-acetylated protein antibodies in the blood sample. ACPAs are autoantibodies with different isotype usage (i.e., IgG, IgA, IgM) that recognize the nonessential amino acid citrulline in proteins. Citrulline is formed as a result of posttranslational modification (citrullination/deimination) of arginine. APCAs present at the early preclinical stage of RA have predictive value of developing full RA. The presence of APCA in established RA can be used to predict disease severity. Detection of ACPAs in body fluids can be assessed by enzyme-linked immunosorbent assay (ELISA) using cyclic citrullinated peptide (CCP) fragments of proteins. Similarly, anti-homocitrullinated and anti-acetylated protein antibodies can also be different isotypes and may be present in early RA.

IgG Epitopes in Covid-19

In infection, RFs are thought to bind to pathogen-antibody immune complexes, or possibly pathogens directly in a cross-reactive manner, to enhance pathogen neutralization and clearance. Without being held to theory, it is believed that RF improves outcomes in COVID-19. In 51 UW Health hospitalized COVID-19 patients who received COVID-19 convalescent plasma, 0% of patients who received plasma with high levels of RF died compared to 16% for low RF plasma, with hospitalization length of stay of 7 versus 16 days, respectively ($p<0.05$). The IgG epitopes of IgG bound in COVID-19 include:

```
                                  (SEQ ID NO: 25)
DKTHTCPPCPAPELLG

                                  (SEQ ID NO: 27)
KDTLMISRTPEVTCVV

                                  (SEQ ID NO: 28)
RDELTKNQVSLTCLVK

                                  (SEQ ID NO: 29)
LTVDKSRWQQGNVFSC
```

Also included herein are peptides that are homologous to the peptides of SEQ ID NOs. 25 and 27-29, such as peptides with 1-6, 1-5, 1-4, 1-3, or 1-2 variant amino acids so long as the peptides can detect bound IgA, IgM, IgG1-4, and/or IgE antibodies in a standard ELISA assay.

In an aspect, the IgG epitope peptides do not comprise a full-length IgG constant region, for example, the epitope peptide comprises 10 to 100 or more contiguous amino acids of an IgG constant region. In a further aspect, the IgG epitope peptides are conjugated to a ligand, a detectable label, or a combination thereof. Ligands and detectable labels are described below.

Also included herein are supports and devices comprising the IgG epitope peptides. Supports and devices are described below.

In an aspect, a method of testing a body fluid or tissue sample from a subject comprises contacting the body fluid or tissue sample with a peptide of SEQ ID NOs. 25 or 27-29 and detecting complexes of the peptide and antibodies in the blood sample.

Convalescent plasma is plasma from people who've recovered from an illness such as COVID-19. Convalescent plasma therapy may be given to people with COVID-19 who are in the hospital and are early in their illness or have a weakened immune system. Convalescent plasma may reduce the severity of disease or length of disease. Convalescent plasma has provided mixed results in the treatment of COVID-19. Methods of screening convalescent plasma to identify efficacious convalescent plasma would improve the success of treatment as the presence of RF in convalescent plasma appeared to correlate with a shortened hospital stay.

In an aspect, a method of screening convalescent plasma from a subject recovered from COVID-19 comprises contacting a convalescent plasma sample from the subject with a peptide of SEQ ID NO. 25, 27-29, and detecting complexes of the peptide and antibodies in the convalescent plasma sample, wherein convalescent plasma containing detectable complexes is selected. The method may further comprise the selected convalescent plasma comprising an anti-SARS-CoV-2 IgG antibody content above the 25th percentile.

In an aspect, an assay combines the RA and COVID-19 peptides. In an aspect, a substrate or device comprises peptides of SEQ ID NOs. 1, 2, 4, 5, 7-10, 12, 13, 15-18, 20-23, and/or 25-29, or a variant with 1-6 variant amino acids at positions wherein the variant peptide detects bound IgA, IgM, IgG1-4, IgE antibodies, or a combination thereof, in an ELISA assay. Such an assay could be used to evaluate RFs in a biological sample from any individual to help diagnose and differentiate between pre-clinical RA, RA, Sjogren's disease, lupus, smokers, and recent infection like COVID-19.

Ligands and Detectable Labels

The IgG epitope peptides described herein can be conjugated to a ligand, such as biotin (e.g., via a cysteine or lysine residue). Attachment to ligands, such as biotin, can be useful for associating the peptide with ligand receptors, such as avidin, streptavidin, polymeric streptavidin, or neutravidin. Avidin, streptavidin, polymeric streptavidin, or neutravidin, in turn, can be linked to a signaling moiety (e.g., an enzyme, such as horseradish peroxidase (HRP) or alkaline phosphatase (ALP) or beta-galactosidase (beta-GAL) or another moiety that can be visualized. Alternatively, the peptides can be conjugated to avidin, streptavidin, polymeric streptavidin, or neutravidin as the ligand, thereby facilitating the association of the peptides with as biotin and any moiety (e.g., signaling moiety) or solid substrate attached thereto. Examples of other ligand-receptor pairs are well-known in the art and can similarly be used.

Exemplary ligands that are carrier proteins include serum albumin, immunoglobulin Fc domain, keyhole limpet hemocyanin (KLH), enzymes (e.g., horse radish peroxidase (HRP), beta-galactosidase, glutathione-S-transferase, alkaline phosphatase), maltose-binding protein (MBP), a histidine tag, and the like. The conjugation can be achieved by means of, e.g., a peptide bond. For example, peptides and fusion partners can be fusion proteins and can be directly fused in-frame or can comprise a peptide linker, as discussed above in the context of additional N-terminal and C-terminal peptide sequences.

The ligand can comprise a lipophilic molecular group. As used herein the term "lipophilic molecular group" refers to a lipid moiety, such as a fatty acid, glyceride or phospholipid which when coupled to a therapeutic molecule, increases its lipophilicity. The lipophilic molecular group can be attached to the therapeutic molecule through an ester bond. Examples of such modifications include, among others, esterification, or amidation of the hydroxy-, amino-, or carboxylic acid-groups of the polypeptide. Lipophilic molecular groups can comprise lipid moieties such as fatty acid, glyceride or phospholipids.

The term "detectable label" as used herein is a molecule that is conjugated directly or indirectly to a probe (e.g., peptide) to generate a "labeled" probe. The label may be detectable by itself (e.g., radioisotope labels, fluorescent agent or chemiluminescent agent) or, in the case of an enzymatic label, may catalyze chemical alteration of a substrate compound or composition that is detectable (e.g., avidin-biotin).

The term "conjugated" refers to any method known in the art for functionally connecting moieties (such as detectable agent, carrier peptide), including, without limitation, recombinant fusion, covalent bonding, disulfide bonding, ionic bonding, hydrogen bonding, and electrostatic bonding.

Solid Support and Devices

The peptides described herein may be attached to or immobilized on a solid support. The attachment can be covalent or non-covalent and can be facilitated by a moiety associated with the peptide that enables covalent or non-covalent binding, such as a moiety that has a high affinity to a component attached to the carrier, support or surface. For example, the peptide can be associated with a ligand, such as biotin, and the component associated with the surface can be a corresponding ligand receptor, such as avidin. In some aspects, the peptide can be associated with a fusion partner, e.g., bovine serum albumin (BSA), which facilitates the attachment of the peptide to a substrate. In other aspects, the peptides are attached to or immobilized on a substrate via a metallic nanolayer such as cadmium, zinc, mercury, or a noble metal, such as gold, silver, copper, and platinum. The peptide can be attached to or immobilized on the substrate either prior to or after the addition of a sample containing antibody during an immunoassay.

In aspects, the substrate is a bead, such as a colloidal particle (e.g., a colloidal nanoparticle made from gold, silver, platinum, copper, cadmium, metal composites, other soft metals, core-shell structure particles, or hollow gold nanospheres) or other type of particle (e.g., a magnetic bead or a particle or nanoparticle comprising silica, latex, polystyrene, polycarbonate, polyacrylate, or PVDF). Such particles can comprise a label (e.g., a colorimetric, chemiluminescent, or fluorescent label) and can be useful for visualizing the location of the peptides during immunoassays. In some aspects, a terminal cysteine of a peptide may be used to bind the peptide directly to the nanoparticles made from gold, silver, platinum, copper, cadmium, metal composites, or other soft metals, or metallic nanoshells (e.g., gold hollow spheres, gold-coated silica nanoshells, and silica-coated gold shells).

In an aspect the substrate is a dot blot or a flow path in a lateral flow immunoassay device. For example, the peptides can be attached or immobilized on a porous membrane, such as a PVDF membrane (e.g., an Immobilon™ membrane), a nitrocellulose membrane, polyethylene membrane, nylon membrane, or a similar type of membrane.

In another aspect, the substrate is a flow path in an analytical or centrifugal rotor. In other aspects, the substrate is a tube or a well, such as a well in a plate (e.g., a microtiter plate) suitable for use in an ELISA assay. Such substrates can comprise glass, cellulose-based materials, thermoplastic polymers, such as polyethylene, polypropylene, or polyester, sintered structures composed of particulate materials (e.g., glass or various thermoplastic polymers), or cast membrane film composed of nitrocellulose, nylon, polysulfone, or the like. A substrate can be sintered, fine particles of polyethylene, commonly known as porous polyethylene. All of these substrate materials can be used in suitable shapes, such as films, sheets, or plates, or they may be coated onto or bonded or laminated to appropriate inert carriers, such as paper, glass, plastic films, or fabrics. Suitable methods for immobilizing peptides on solid phases include ionic, hydrophobic, covalent interactions and the like.

Accordingly, in another aspect, the invention provided herein are devices. The devices may be useful for performing an immunoassay. For example, in aspects, the device is a lateral flow immunoassay device. In some aspects, the device is a slide comprised of a plurality of beads to which a peptide or population of peptides is attached. In other embodiments, the device is an analytical or centrifugal rotor. In other aspects, the device is a dot blot, slot blot, or Western blot. In other aspects, the device is a tube or a well, e.g., in a plate suitable for an ELISA assay. In still other aspects, the device is an electrochemical sensor, an optical sensor, or an opto-electronic sensor.

Exemplary detection methods include detection of an agent which is tagged, directly or indirectly, with a colorimetric assay (e.g., for detection of HRP or beta-galactosidase activity), visual inspection using light microscopy, immunofluorescence microscopy, including confocal microscopy, or by flow cytometry (FACS), autoradiography (e.g., for detection of a radioactively labeled agent), electron microscopy, immunostaining, subcellular fractionation, and the like. In an aspect, a radioactive element (e.g., a radioactive amino acid) is incorporated directly into a peptide chain; in another embodiment, a fluorescent label is associated with a peptide via biotin/avidin interaction, association with a fluorescein conjugated antibody, or the like. In an embodiment, a detectable specific binding partner for the antibody is added to the mixture. For example, the binding partner can be a detectable secondary antibody or other binding agent (e.g., protein A, protein G, protein L or combinations thereof) which binds to the first antibody. This secondary antibody or other binding agent can be labeled, e.g., with a radioactive, enzymatic, fluorescent, luminescent, metallic nanoparticle or metallic nanoshell (e.g., colloidal gold), or other detectable label, such as an avidin/biotin system. In another embodiment, the binding partner is a peptide of the invention, which can be conjugated directly or indirectly (e.g., via biotin/avidin interaction) to an enzyme, such as horseradish peroxidase or alkaline phosphatase or other signaling moiety. In such embodiments, the detectable signal is produced by adding a substrate of the enzyme that produces a detectable signal, such as a chromogenic, fluorogenic, or chemiluminescent substrate.

A "detection system" for detecting bound peptide may comprise a detectable binding partner, such as an antibody specific for the peptide. In one embodiment, the binding partner is labeled directly. In another embodiment, the binding partner is attached to a signal generating reagent, such as an enzyme that, in the presence of a suitable substrate, can produce a detectable signal. A surface for immobilizing the peptide may optionally accompany the detection system.

In an aspect, the detection procedure comprises visibly inspecting the antibody-peptide complex for a color change or inspecting the antibody-peptide complex for a physical-chemical change. Physical-chemical changes may occur with oxidation reactions or other chemical reactions. They may be detected by eye, using a spectrophotometer, or the like.

One assay format is a lateral flow immunoassay format. Antibodies to human or animal (e.g., dog, mouse, deer, etc.) immunoglobulins, or staph A, G, or L proteins, can be labeled with a signal generator or reporter (e.g., colloidal gold) that is dried and placed on a glass fiber pad (sample application pad or conjugate pad). The diagnostic peptide is immobilized on membrane, such as nitrocellulose or a PVDF (polyvinylidene fluoride) membrane (e.g., an Immobilon™ membrane). When a solution of sample (blood, serum, etc.) is applied to the sample application pad (or flows through the conjugate pad), it dissolves the labeled reporter, which then binds to all antibodies in the sample. The resulting complexes are then transported into the next membrane (PVDF or nitrocellulose containing the diagnostic peptide) by capillary action. If antibodies against the diagnostic peptide are present, they bind to the diagnostic peptide striped on the membrane, thereby generating a signal (e.g., a band that can be seen or visualized). An additional antibody specific to the labeled antibody or a second labeled antibody can be used to produce a control signal.

An alternative format for the lateral flow immunoassay comprises the peptides being conjugated to a ligand (e.g., biotin) and complexed with labeled ligand receptor (e.g., streptavidin-colloidal gold). The labeled peptide complexes can be placed on the sample application pad or conjugate pad. Anti-human IgG/IgM/IgA or anti-animal (e.g., dog, mouse, deer) IgG/IgM/IgA antibodies or other peptides of the invention are immobilized on a membrane, such as nitrocellulose of PVDF, at a test site (e.g., a test line). When sample is added to the sample application pad, antibodies in the sample react with the labeled peptide complexes such that antibodies that bind to peptides of the invention become indirectly labeled. The antibodies in the sample are then transported into the next membrane (PVDF or nitrocellulose containing the diagnostic peptide) by capillary action and bind to the immobilized anti-human IgG/IgM/IgA or anti-animal IgG/IgM/IgA antibodies (or protein A, protein G, protein A/G fusion proteins, protein L, or combinations thereof) or immobilized peptides of the invention. If any of the sample antibodies are bound to the labeled peptides of the invention, the label associated with the peptides can be seen or visualized at the test site.

Another assay for the screening of blood products or other physiological or biological fluids is an enzyme linked immunosorbent assay, i.e., an ELISA. Typically, in an ELISA, isolated peptides or mixtures or populations of peptides of the invention are adsorbed to the surface of a microtiter well directly or through a capture matrix (e.g., an antibody, or avidin to bind biotin-labeled peptides). Residual, non-specific protein-binding sites on the surface are then blocked with an appropriate agent, such as bovine serum albumin (BSA), heat-inactivated normal goat serum (NGS), or BLOTTO (a buffered solution of nonfat dry milk which also contains a preservative, salts, and an antifoaming agent). The well is then incubated with a biological sample suspected of containing RF. The sample can be applied neat, or more often it can be diluted, usually in a buffered solution which contains a small amount (0.1-5.0% by weight) of protein, such as BSA, NGS, or BLOTTO. After incubating for a sufficient length of time to allow specific binding to occur, the well is washed to remove unbound protein and then incubated with an optimal concentration of an appropriate anti-immunoglobulin antibody (e.g., for human subjects, an anti-human immunoglobulin (αHuIg) from another animal, such as dog, mouse, cow, etc.) or another peptide that is conjugated to an enzyme or other label by standard procedures and is dissolved in blocking buffer. The label can be chosen from a variety of enzymes, including horseradish peroxidase (HRP), beta-galactosidase, alkaline phosphatase (ALP), glucose oxidase, etc. Sufficient time is allowed for specific binding to occur again, then the well is washed again to remove unbound conjugate, and a suitable substrate for the enzyme is added. Color is allowed to develop and the optical density of the contents of the well is determined visually or instrumentally (measured at an appropriate wavelength). The cutoff OD value may be defined as the mean OD+3 standard deviations (SDs) of at least 50 serum samples collected from healthy individuals without RFs, or by other such conventional definitions. In the case of a very specific assay, OD+2 SD can be used as a cutoff value.

In one embodiment of an ELISA, a peptide is immobilized on a surface, such as a ninety-six-well ELISA plate or equivalent solid phase that is coated with streptavidin or an equivalent biotin-binding compound, such as avidin or neutravidin, at an optimal concentration in an alkaline coating buffer and incubated at 4° C. overnight. After a suitable number of washes with standard washing buffers, an optimal concentration of a biotinylated form of a peptide, dissolved in a conventional blocking buffer, is applied to each well. A sample is then added, and the assay proceeds as above. Conditions for performing ELISA assays are well-known in the art.

In another embodiment of an ELISA, a peptide or a mixture of peptides is immobilized on a surface, such as a ninety-six-well ELISA plate or equivalent solid phase via a fusion partner, e.g., BSA or MAPS. A sample is then added, and the assay proceeds as above.

An alternative format for the ELISA assay features the peptide(s) being attached (e.g., fused) to an appropriate enzyme, such as HRP. Steps for carrying out such an ELISA include: coating the wells of a plate with anti-dog, anti-cat, or anti-human IgG/IgM/IgA; incubating samples suspected of containing antibodies to the peptide with the immobilized anti-species IgG/IgM/IgA; removing unreacted sample and washing the wells with a suitable wash buffer; applying enzyme-coupled (e.g., HRP-coupled) peptide of the invention and allowing it to react with any captured RF; and visualizing the enzyme-coupled peptide by applying an appropriate enzyme substrate (e.g., TMB).

The invention is further illustrated by the following non-limiting examples.

EXAMPLES

Methods

Human Subjects: Human subjects research was approved by the University of Wisconsin (UW) Institutional Review Board and complied with the Helsinki Declaration. Most sera were obtained from the UW Rheumatology Biorepository, which includes rheumatoid arthritis, systemic lupus erythematosus, Sjögren's disease (SjD), spondyloarthropathy, and controls (including current and never smokers) collected prior to 2019. Subjects were ≥18 years old. All subjects with rheumatic disease were confirmed to have that disease by a rheumatologist. Sera from COVID-19 patients were obtained from the UW COVID-19 Biorepository and all COVID-19 subjects had a positive PCR test for SARS-COV-2 infection. Controls were matched by age and gender and carried none of the following diagnoses: RA, lupus, Sjögren's disease, scleroderma, psoriasis, psoriatic arthritis, ankylosing spondylitis, reactive arthritis, ulcerative colitis, Crohn's disease, multiple sclerosis, type I diabetes, hematologic malignancy, or past COVID-19. Plasma samples for the pre-clinical RA experiments were acquired from the University of Colorado in Denver (anti-CCP− controls, anti-CCP+ subjects who did not develop RA, anti-CCP+ subjects who developed RA).

High Density Peptide Array: A high density peptide array (Roche Nimblegen, Madison, USA) was used to detect serum IgG, IgM, and IgA that bound to overlapping 12-16 amino acid peptides derived from the constant region of the heavy chains of IgG1 (Uniprot P01857), IgG2 (P01859), IgG3 (P01860), and IgG4 (P01861) as described in the art. Peptides were included in native form, and in the case of FIG. 1, with all arginines replaced by citrullines, and with all lysines replaced by homocitrullines.

Monoclonal AMPA (mAMPA): Generation of the human monoclonal AMPAs from single B cells from RA patients has previously been described in the art. Clones 1325:07E07 and 1325:04C03 were derived from synovial plasma cells and clones 37CEPT1G09, 14CFCT3G09 and 37CEPF2C05 were derived from blood memory B cells. The monoclonal antibodies were recombinantly expressed as hIgG1, purified and extensively quality controlled. All AMPA clones bind CCP2 and multiple citrullinated peptides without native peptide reactivity and with reactivity against homocitrullinated antigens ranging from very limited to extensive. The negative control clone 1362:01E02 has not displayed any reactivity to any post translational modifications or control antigens.

Post-translational modification of IgG Fc: IgG Fc (MilliporeSigma, Burlington, USA) was depleted of contaminating IgM and light chain using streptavidin magnetic beads (Thermo Fisher Scientific, Waltham, USA) coated with biotin-conjugated goat IgG anti-human IgM, goat IgG anti-human kappa and goat IgG anti-human lambda (Southern Biotech, Birmingham, USA). IgG Fc was citrullinated by treating with 2 μg of peptidylarginine deiminase (PAD) 2 and PAD4 per 1 mg of IgG Fc in a buffer of 100 mM Tris-HCl pH7.5, 1 mM DTT, and 5 mM CaCl2). IgG Fc was homocitrullinated by treating with 0.1M KOCN in $dH_2O$, stopping the reaction with 0.15 M Tris pH 8.8.

Enzyme Linked Immunosorbent Assay (ELISA): For peptide ELISA, plates were coated with 5 μg/ml streptavidin (Thermo Fisher Scientific) for 1 hour at room temperature (RT) or overnight at 4 degrees Celsius, washed with PBS, then coated with 0.1-1.0 μM of peptide conjugated to biotin at the C terminus (Biomatik, Kitchener, Canada or Peptide2.0, Chantilly, VA, USA) for 1 hour at RT. Selected peptides are listed in Table 2. For IgG Fc ELISA, plates were coated overnight at 4° C. with 10 μg/ml IgG Fc in PBS in 4 forms: treated with PADs in buffer, treated with 0.1M KOCN in $dH_2O$, diluted in citrullination buffer, diluted in $dH_2O$. After washing with PBS, plates were blocked for 1 hour to overnight at RT with 5% non-fat dried milk in 0.2% Tween 20 in PBS (serum ELISA block) or 1% BSA in PBS (mAMPA ELISA block without 0.1% Tween 20). Sera diluted 1:100, 1:200 or 1:2000 in serum ELISA block or 1 μg/ml mAMPAs in mAMPA ELISA block were applied to plates overnight at 4° C. After washing, plates were incubated with mouse monoclonal anti-human IgG (clone JDC-10), IgM, or IgA conjugated to horse radish peroxidase diluted 1:5000 in serum ELISA block or goat anti-human lambda and anti-human kappa IgG conjugated to horse radish peroxidase (Southern Biotech) diluted 1:5000 in mAMPA ELISA block. After one hour at RT, plates were washed, developed with 3,3',5,5'-tetramethylbenzidine (Thermo Fisher Scientific), then stopped with 0.18 M sulfuric acid. Plates were read on a FilterMAX F3 (Molecular Devices, San Jose, USA) at 450 and 562, with 562 values subtracted from 450 values for each sample. For each sample, absorbance values for uncoated wells were subtracted from peptide- or Fc-coated wells to exclude non-specific binding, and absorbance values for PAD-containing buffer were subtracted from wells coated with PAD-treated IgG Fc to exclude anti-PAD reactivity.

TABLE 2

| SELECTED PEPTIDES | |
|---|---|
| P01857-11 | LAPSSKSTSGGTAALGC<br>SEQ ID NO: 1 |
| P01857-11J | LAPSSJSTSGGTAALGC<br>SEQ ID NO: 2 |
| P01857-80 | TYICNVNHKPSNTKVDKKVEPKSC<br>SEQ ID NO: 4 |
| P01857-80J | TYICNVNHJPSNTJVDJJVEPJSC<br>SEQ ID NO: 5 |
| P01857-109 | CPPCPAPELLGGPSV<br>SEQ ID NO: 26 |
| P01857-167 | VHNAKTKPREEQYNSTYRVVSV<br>SEQ ID NO: 7 |
| P01857-167B | VHNAKTKPBEEQYNSTYBVVSV<br>SEQ ID NO: 8 |
| P01857-167J | VHNAJTJPREEQYNSTYRVVSV<br>SEQ ID NO: 9 |
| P01857-167JB | VHNAJTJPBEEQYNSTYBVVSV<br>SEQ ID NO: 10 |
| P01857-202 | YKCKVSNKALPAP<br>SEQ ID NO: 12 |
| P01857-202J | YJCJVSNJALPAP<br>SEQ ID NO: 13 |
| P01857-219 | ISKAKGQPREPQVYTLPPSRDEL<br>SEQ ID NO: 15 |
| P01857-219B | ISKAKGQPBEPQVYTLPPSBDEL<br>SEQ ID NO: 16 |
| P01857-219J | ISJAJGQPREPQVYTLPPSRDEL<br>SEQ ID NO: 17 |
| P01857-219JB | ISJAJGQPBEPQVYTLPPSBDEL<br>SEQ ID NO: 18 |
| P01857-289 | LYSKLTVDKSRWQQGNVFS<br>SEQ ID NO: 20 |
| P01857-289B | LYSKLTVDKSBWQQGNVFS<br>SEQ ID NO: 21 |
| P01857-289J | LYSJLTVDJSRWQQGNVFS<br>SEQ ID NO: 22 |
| P01857-289BJ | LYSJLTVDJSBWQQGNVFS<br>SEQ ID NO: 23 |
| P01857-104 | DKTHTCPPCPAPELLG<br>SEQ ID NO: 25 |
| P01857-131 | KDTLMISRTPEVTCVV<br>SEQ ID NO: 27 |
| P01857-238 | RDELTKNQVSLTCLVK<br>SEQ ID NO: 28 |
| P01857-293 | LTVDKSRWQQGNVFSC<br>SEQ ID NO: 29 |

For some experiments, each plate included a standard curve of purified human IgG ranging from 0.0169 to 1000 ng/ml. To generate the human IgG standard curve, wells were coated with streptavidin as above, followed by biotin-labeled goat IgG anti-human lambda and kappa (Southern Biotech) capture antibodies at a 1:5000 dilution. Following a blocking step, serially diluted purified human IgG (Bethyl Laboratories, Montgomery, USA) in blocking buffer was added to the wells. The serially diluted human IgG was detected using the same method as above. The background-corrected absorbance values for the patient serum samples were converted to ng/ml of human IgG by applying a four parameter nonlinear curve fit to the wells containing the human IgG standards (elisaanalysis.com). In other experiments, normalized absorbance was reported and not Ig concentration.

Statistical analysis: To avoid making distributional assumptions about the array measurements, nonparametric statistical tests were used. ELISA data for disease groups versus controls were compared by Mann-Whitney or Kruskal-Wallis tests. Analyses were performed using Prism (GraphPad Software, San Diego, CA, USA) and a p-value less than 0.05 was considered significant.

Example 1: IgG Epitopes Bound in RA

To evaluate IgG epitopes bound in RA and other rheumatic diseases, IgG binding to every 12 amino acid linear peptide derived from the constant region of the heavy chain of human IgG1-4 was quantified using a high density peptide array and sera from patients diagnosed with RA (anti-CCP+RF+ and anti-CCP-RF−), lupus, Sjögren's disease (anti-SSA+ and anti-SSA−), or spondyloarthropathy with age- and gender-matched control subjects. As shown in FIG. 1, anti-CCP+RF+RA serum IgG bound strongly to multiple citrulline- and homocitrulline-containing peptides of IgG1 with minimal binding to corresponding arginine- and lysine-containing native peptides. Similar results were seen for IgG2, IgG3, and IgG4. IgG from other diseases displayed very limited binding to linear IgG-derived peptides with anti-SSA+Sjögren's disease and spondyloarthropathy serum IgG binding to native peptides in the hinge region. As expected, anti-CCP-RF−RA and anti-SSA-Sjogren's disease had no areas of high binding to IgG-derived peptides.

Figure 2:
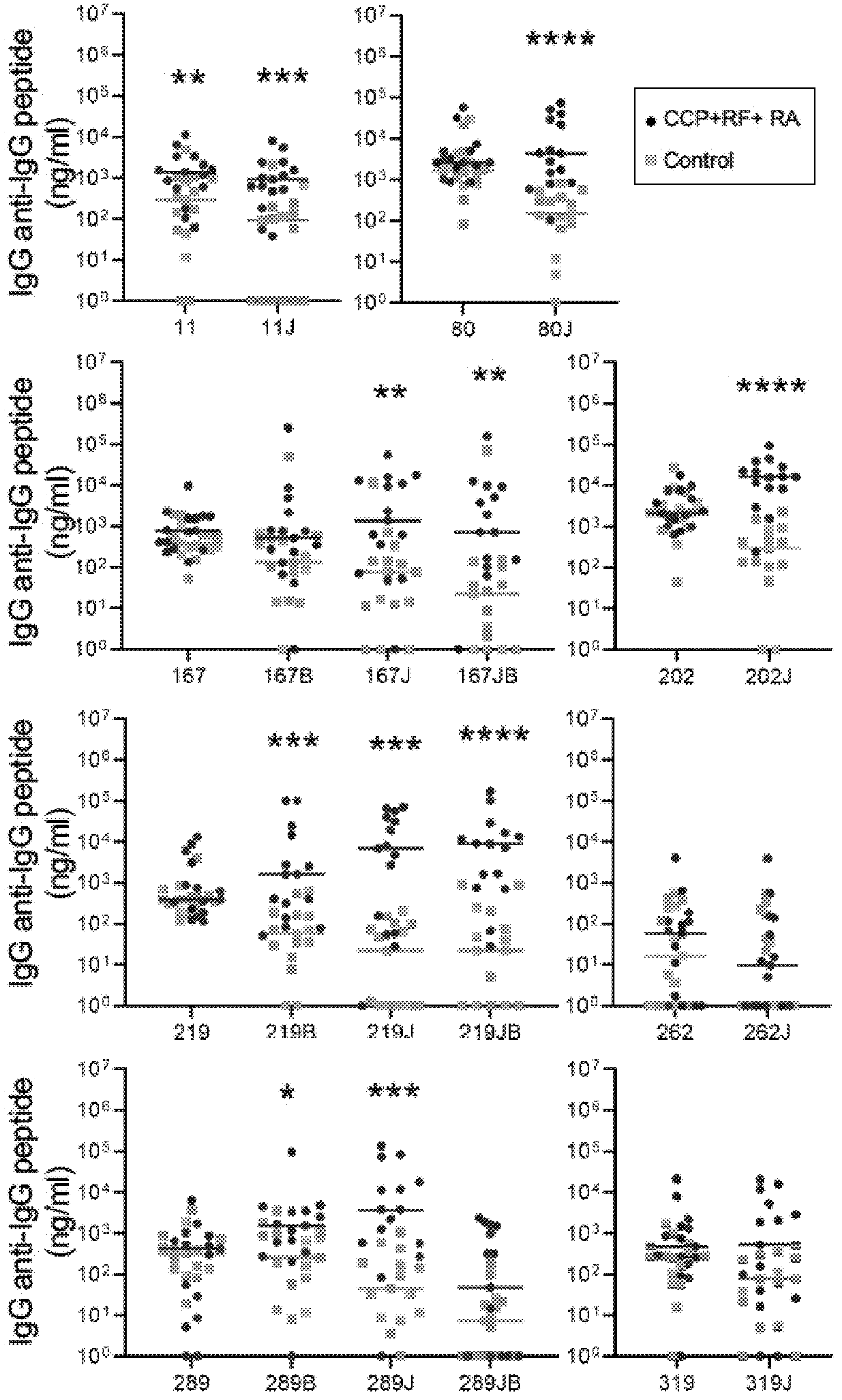
FIG. 2 shows that multiple modified IgG-derived peptides are bound by IgG in anti-CCP+RF+RA. Binding of IgG from anti-CCP+RF+RA and control sera to native, citrulline (B)-containing, homocitrulline (J)-containing, and JB-containing peptides starting at the indicated amino acid position of the constant region of the IgG1 heavy chain was quantified by ELISA (n=15). Anti-CCP+RF+RA was compared to matched controls by Mann-Whitney test, bars indicate median, and *p<0.05, p<0.01, *p<0.001, ****p<0.0001.

Regions of IgG1, the most abundant IgG subclass, were selected that were highly bound in anti-CCP+RF+RA based on the array experiment for further evaluation of IgG binding by ELISA. As shown in FIG. 2, anti-CCP+RF+RA sera bound more greatly than control sera to most of the homocitrulline-containing, citrulline-containing, and dually modified peptides, with only one native peptide bound more in RA than controls. Interestingly, the increased binding in RA as compared to control subjects was due to both increased binding in RA and reduced binding in controls to modified as compared to native versions of those peptides. Also, some subjects had high binding at specific epitopes while others did not. Anti-CCP-RF−RA sera showed no increased binding to any peptide (data not shown).

Figure 3:
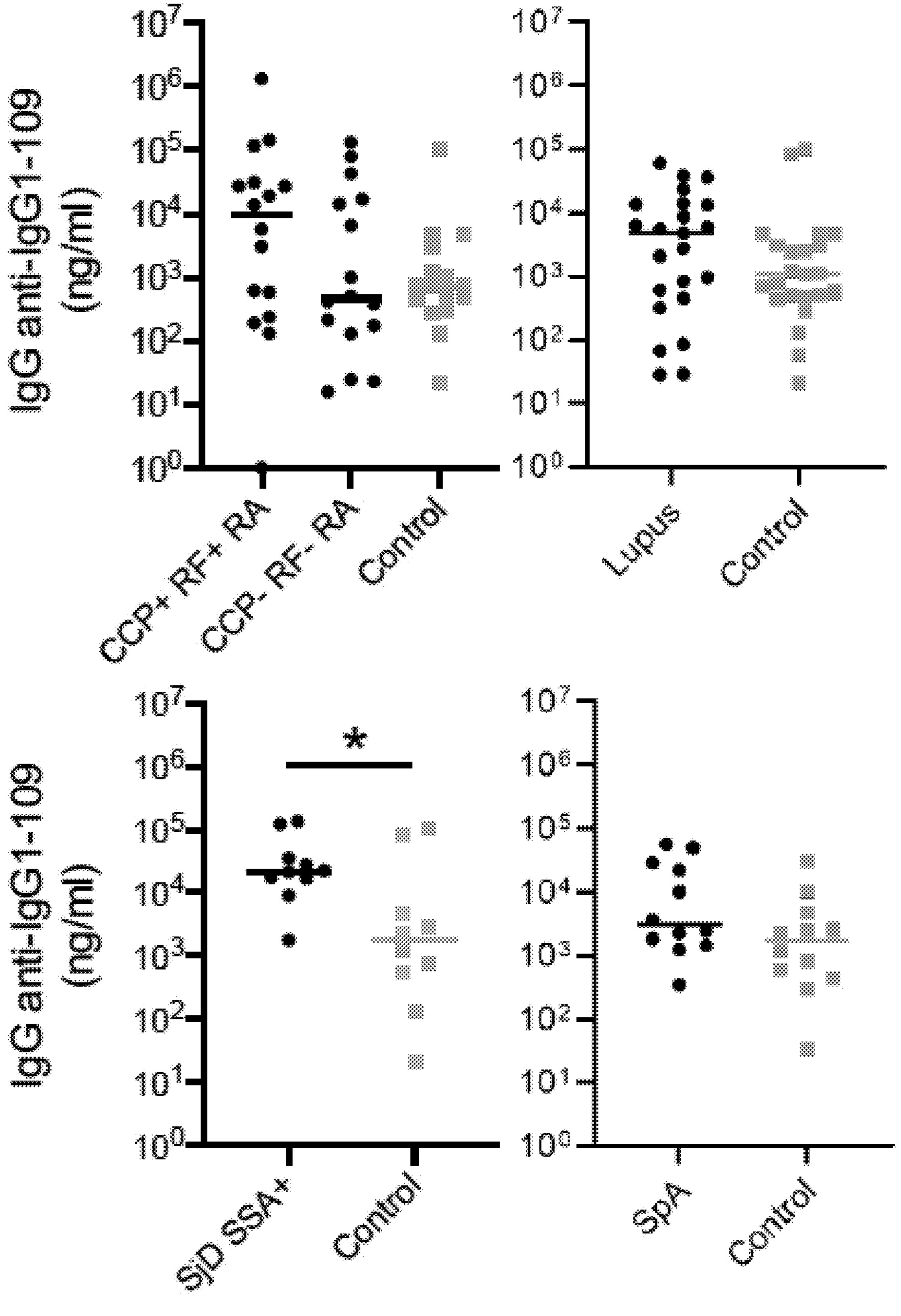
FIG. 3 shows that a native linear peptide from the hinge region of IgG1 is bound in Sjögren's disease. Binding of IgG to a hinge peptide (position 109) was quantified by ELISA for anti-CCP+RF+RA (n=16), anti-CCP-RF−RA (n=16), lupus (n=23), anti-SSA+ primary Sjögren's disease (SjD, n=10), spondyloarthropathy (SpA, n=12), and matched controls. Disease groups were compared to controls by Kruskal-Wallis or Mann-Whitney test, bars indicate median, and *p<0.05.

Next, a peptide from IgG1 in the hinge region starting at position 109, which appeared to be highly bound in non-RA rheumatologic disease by array (FIG. 1), was evaluated. As shown in FIG. 3, anti-SSA+Sjögren's disease serum IgG, but not lupus or spondyloarthropathy serum IgG, had significantly increased binding compared to controls to the hinge peptide. There was a trend towards increased binding in anti-CCP+RF+RA as compared to controls, but no increased binding in anti-CCP-RF−RA (FIG. 3). Together these data demonstrate a wide range of binding to multiple citrulline- and homocitrulline-containing IgG epitopes in anti-CCP+RF+RA with binding to a single linear IgG epitope in Sjögren's disease.

Figure 4A:
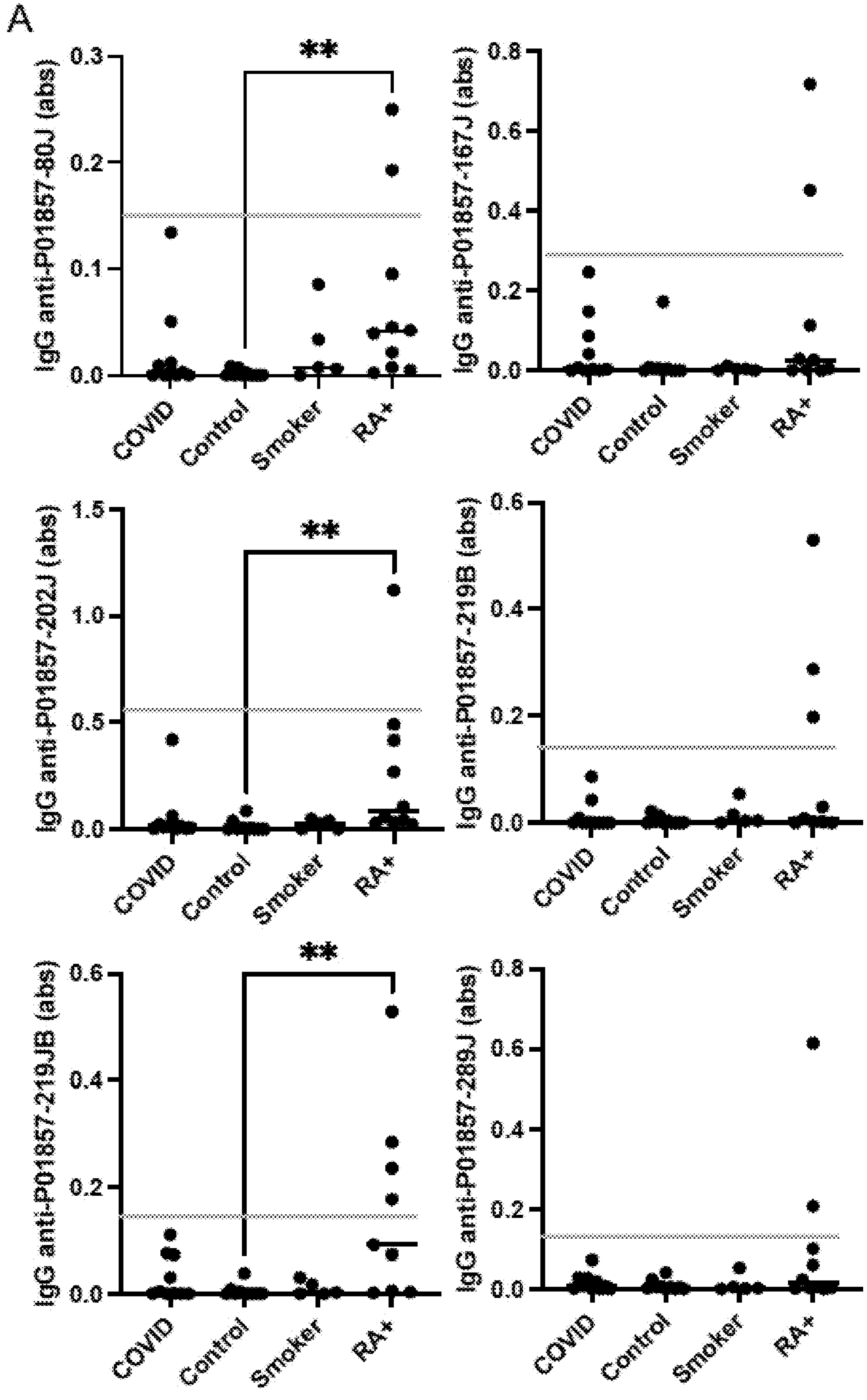
FIGS. 4A-B show that serum IgG and IgA in RA bind to specific IgG1 derived peptides not bound in COVID-19, smokers, or controls. Binding of serum IgG (FIG. 4A) and IgA (FIG. 4B) was quantified by ELISA for subjects 5 weeks post-COVID-19 (n=10), controls (n=10), current smoker controls (n=5), and anti-CCP+RF+RA (n=10) to native, citrulline (B)-containing, homocitrulline (J)-containing, and JB-containing peptides starting at amino acid position 11, 80, 167, 202, 219, and 289 of the constant region of the IgG1 heavy chain. Groups were compared by Kruskal-Wallis test, bars indicate median, gray lines indicate potential cut-offs for positive testing, and *p<0.05, *p<0.01. Only peptides that demonstrate differences in groups are displayed. No peptide with high binding in RA showed high binding for COVID-19 subjects.
Figure 4B:
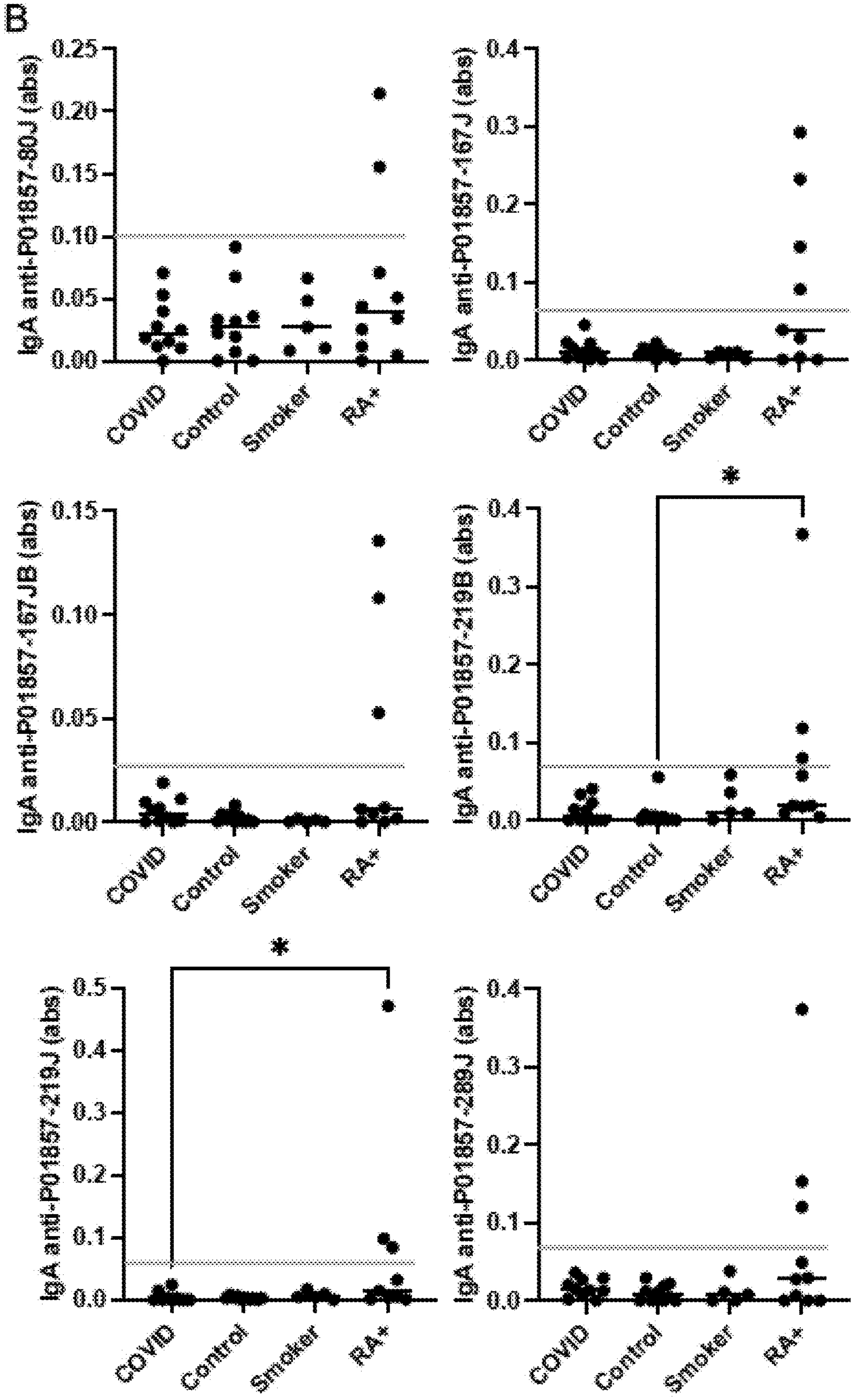

Finally, IgA, IgM, and IgG that bound the citrulline- and homocitrulline-containing IgG1 epitopes bound in RA were evaluated in subjects 5 weeks post-COVID-19 and smokers (in addition to controls and anti-CCP+RF+RA subjects), given the previously reported presence of RFs in smokers and some individuals with infections. For many peptides, particularly for IgM binding, there was no increased binding in any group of subjects (data not shown). However, for several peptides there was increased IgG (FIG. 4A) or IgA (FIG. 4B) binding to the citrulline- and homocitrulline-containing IgG1 epitopes only in RA, and not in COVID-19 or smokers, providing additional evidence that citrulline- and homocitrulline-containing IgG1 epitopes are uniquely bound by Ig in RA.

Figures 5A, 5B:
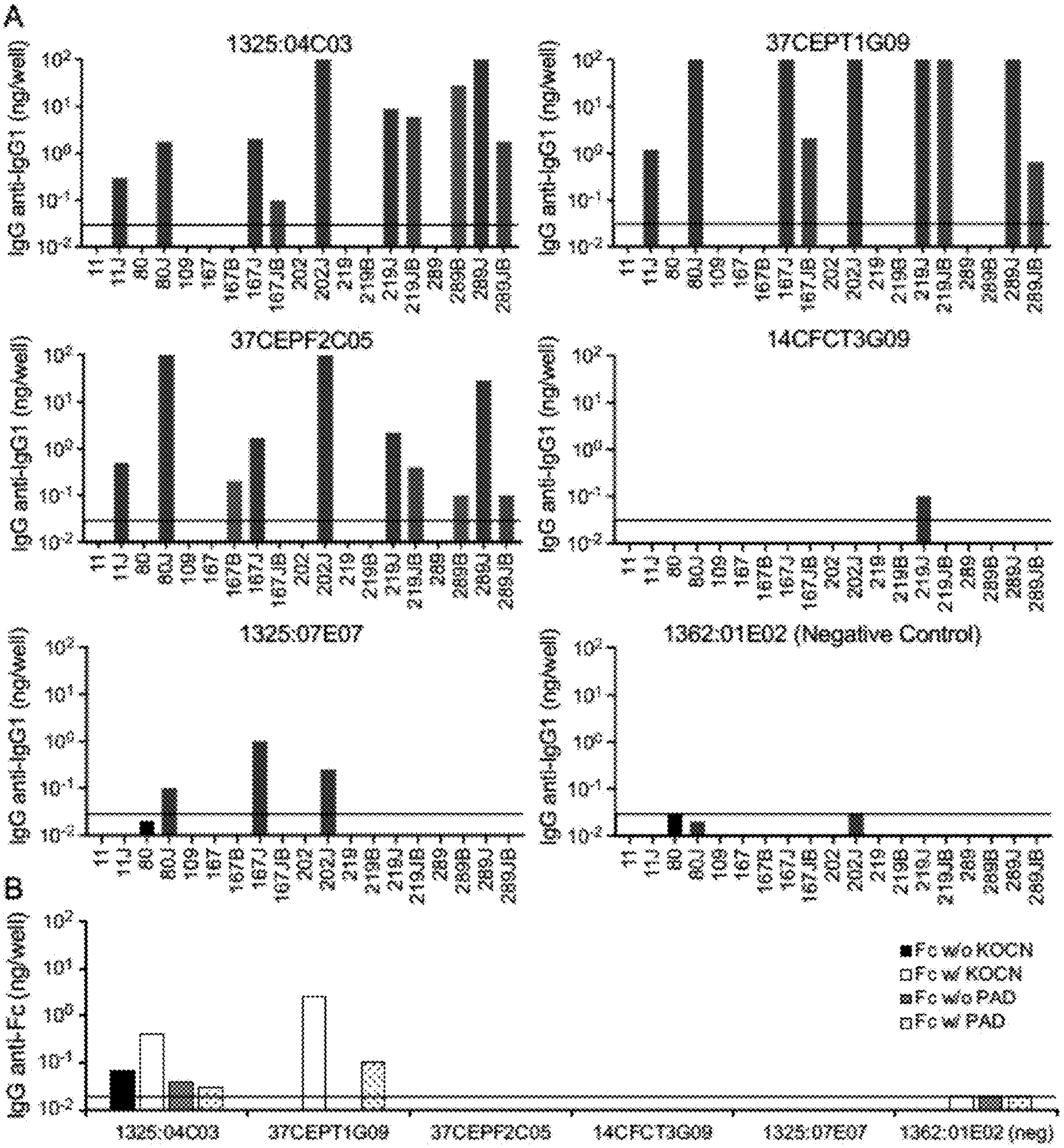
FIGS. 5A and B show that AMPAs bind citrulline (B)- and homocitrulline (J)-containing IgG-derived peptides and modified IgG Fc. Five patient-derived monoclonal AMPAs and one negative control monoclonal antibody were assessed by ELISA for binding to IgG1-derived peptides (FIG. 5A) and human IgG Fc (FIG. 5B) that was unmodified (exposed to buffer alone) or treated with peptidylarginine deiminases (PADs) to citrullinate or KOCN to homocitrullinate. Numbers indicate the location of the first amino acid of the peptide in the constant region of the IgG1 heavy chain. Line indicates highest level of binding detected for the negative control monoclonal antibody.

Given the different IgG epitopes bound in anti-CCP+RF+ RA versus Sjögren's disease and the frequent coexistence of AMPAs and RF in RA, it was next determined if multi-reactive monoclonal AMPAs could bind to the IgG epitopes highly bound in RA. Five patient-derived mAMPAs previously determined to have cross-reactivity against multiple citrulline-containing epitopes, varying levels of homocitrulline reactivity, and no reactivity with native antigens and one negative control monoclonal antibody were evaluated for binding to IgG-derived peptides by ELISA. As shown in FIG. 5A, the three mAMPAs (1325:03C03, 37CEPT1G09 and 37CEPTF2C05) previously shown to have homocitrulline multi-reactivity bound to many modified (including all homocitrulline-containing), but not native, IgG-derived peptides with different patterns among clones. The two mAMPA clones (1325:07E07 and 14CFCT3G09) previously shown to be primarily citrulline-restricted showed very limited binding to IgG-derived peptides. Compared to the extensive binding to homocitrulline-containing peptides, binding to doubly modified peptides was less consistent and binding to citrulline-containing peptides was low. Finally, we evaluated mAMPA binding to native, citrullinated, and homocitrullinated IgG Fc protein. As shown in FIG. 5B, two mAMPAs with high reactivity to modified IgG-derived peptides also bound to IgG Fc, particularly homocitrullinated Fc. Together, these data demonstrate that monoclonal AMPAs, which bind many different modified epitopes, also bind IgG epitopes, bridging the divide between AMPAs and RFs.

Discussion of IgG Epitopes Bound in RA

In this study, IgG binding to all possible linear epitopes of the constant region of IgG heavy chain was evaluated to reveal several key features of autoantibody reactivity in rheumatic disease. First, several homocitrulline-containing IgG epitopes were bound in anti-CCP+RF+RA subjects with a wide range of reactivity (FIG. 2). Similarly, the mAMPAs had different reactivities to IgG epitopes. Homocitrulline-containing epitopes were bound prominently by mAMPAs, but to widely varying extents. Interestingly, only two of five mAMPAs bound to citrulline-containing epitopes, perhaps due to the absence of glycine neighboring the citrullines, a previously identified binding motif for three of the mAMPAs in the study. Minimal citrullination in the case of the Fc protein may have also contributed. Regardless of the cause, these findings demonstrate different AMPA and RF repertoires among RA subjects with strong binding to homocitrullinated and citrullinated epitopes.

In addition to variability in IgG binding among subjects, variability was observed among epitopes. Different citrulline- and homocitrulline-containing epitopes were not bound equally by RA sera and reactivity to citrulline- and homocitrulline-containing epitopes did not guarantee reactivity with dually modified epitopes, supporting the idea that modification alone is insufficient for antibody binding across all individuals.

In contrast to the extensive binding of linear IgG epitopes in anti-CCP+RF+RA, consistent IgG binding was demonstrated to only one linear IgG epitope in one non-RA disease: a hinge region epitope bound in anti-SSA+Sjögren's disease. Conformational epitopes in the hinge and CH2/CH3 regions of IgG have been described in RA, hematologic malignancy, lupus, and healthy individuals. Antibody binding to multiple linear epitopes may be a relatively unique feature of RA, consistent with observed reactivity against structurally disordered citrulline-containing and native epitopes. Of note, this difference in reactivity against some IgG epitopes in RA versus other rheumatic diseases could be leveraged to refine diagnostic testing.

Figure 6:
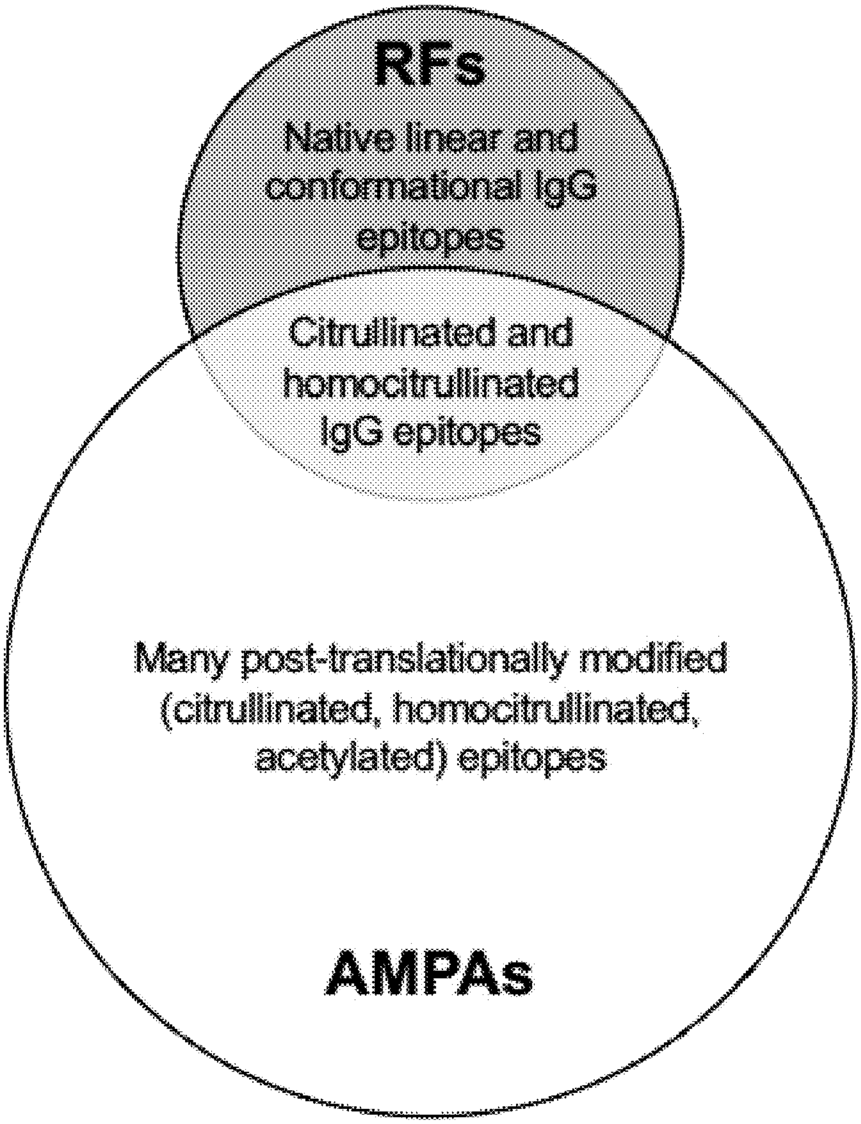
FIG. 6 shows that the reactivities of RFs and AMPAs converge on IgG epitopes. This schematic illustrates the Venn Diagram of RF and AMPA reactivities. RFs bind native linear and conformational IgG epitopes and AMPAs bind many different post-translationally modified epitopes. Antibodies that bind citrulline- and homocitrulline-containing IgG epitopes can be considered both a RF, an antibody that binds to the Fc region of IgG, and an AMPA, an antibody that binds post-translationally modified epitopes.

Taken together, these findings expand and partially merge the reactivities of RFs and AMPAs (FIG. 6). Two linear native epitopes (starting at aa positions 11 and 109) were added to the RF repertoire as well as multiple citrulline- and homocitrulline-containing IgG epitopes to both the RF and AMPA repertoires, positioning IgG as a shared antigen for RFs and AMPAs. The binding of AMPAs to modified IgG epitopes allows for the possibility that IgG, potentially modified, conformationally altered, and/or degraded in vivo, could be a common antigen underlying the development of AMPAs and IgG-RFs in RA. If true, then tolerance might be lost against modified IgG through a shared epitope-related mechanism, leading to AMPAs and IgG-RFs via epitope spreading. This mechanism may not lead to all IgG-RF, including IgG-RF in lupus, a disease without citrulline reactivity. Moreover, this mechanism would not lead to IgM-RF, a major portion of RF in RA, which may be a non-specific response to inflammation. Consistent with this idea, IgM from anti-CCP+RF−, anti-CCP-RF+, and anti-CCP+RF+RA patients had limited binding to citrulline- and homocitrulline-containing IgG epitopes as evaluated by a previous peptide array. Alternatively, AMPAs, perhaps with limited multi-reactivity, could develop first, followed by the development of anti-modified IgG antibodies and later RF possibly via epitope spreading, which would be consistent with the detection of ACPAs prior to RFs in pre-clinical RA, as well as the absence of anti-modified IgG antibodies in anti-CCP+RF−RA. Without being held to theory, it is believed that the observation that IgG is a common antigen for RF and AMPAs could underly the frequent occurrence of AMPAs and IgG-RF in RA.

In summary, we discovered new IgG epitopes in rheumatic disease and demonstrated that IgG epitopes are bound by AMPAs, in addition to RFs. These findings provide new insights into the loss of tolerance against IgG and the development of autoantibodies in RA and other rheumatic diseases.

Example 2: IgG Epitopes Bound in Covid-19

Figure 7A:
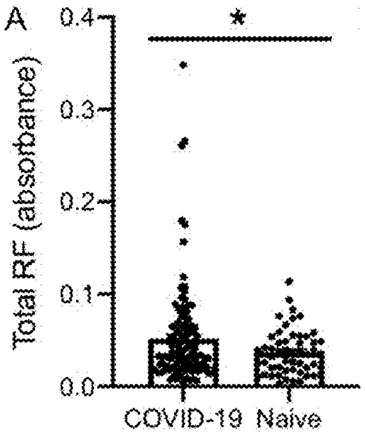
FIGS. 7A and B show rheumatoid factors in COVID-19 convalescent subjects.
Figure 7B:
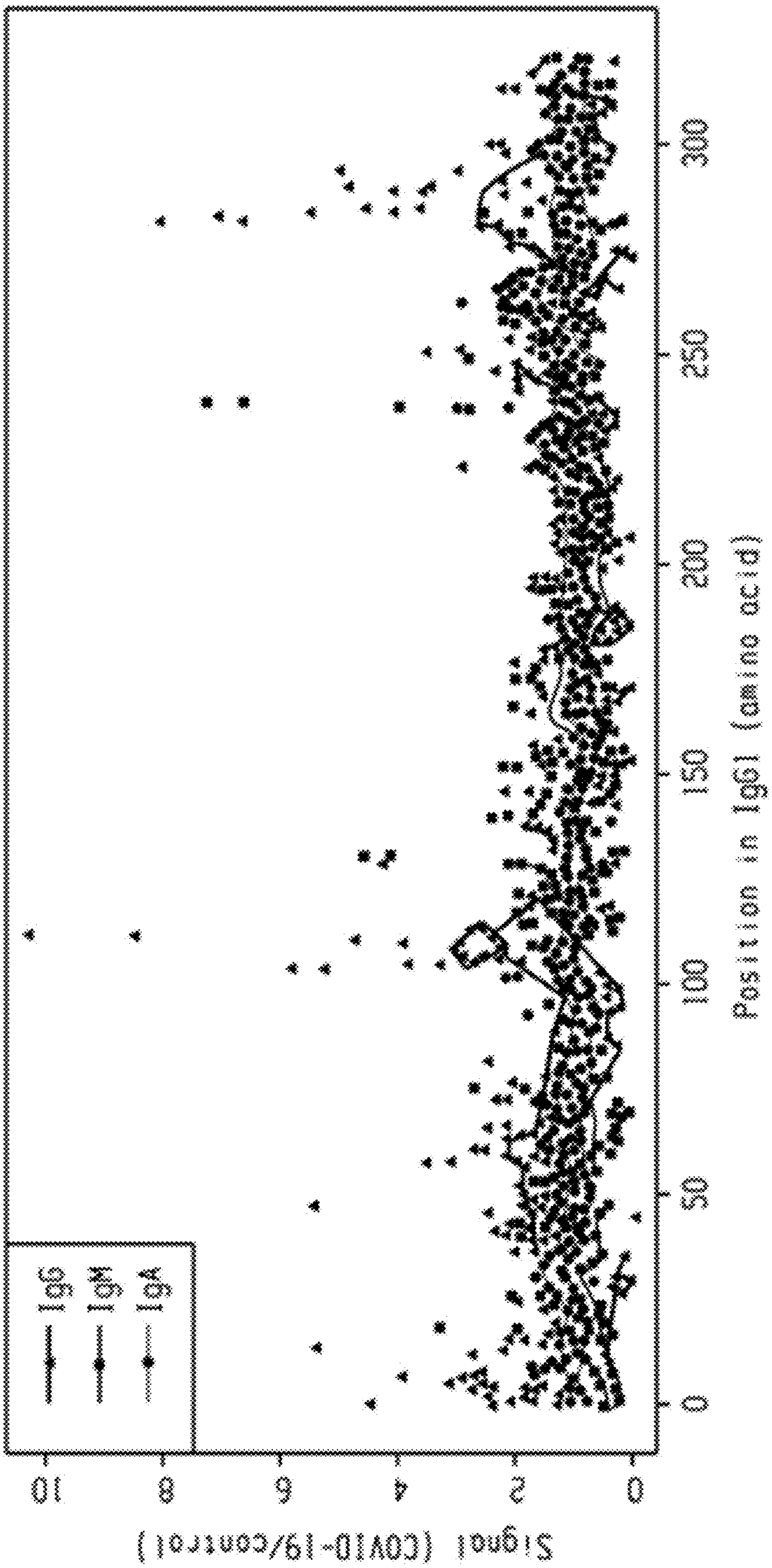
FIG. 7B. To identify linear epitopes of IgG bound by antibodies, sera from 40 of these COVID-19 convalescent subjects and 20 of the COVID-19 naïve subjects were subjected to a high density peptide array in which all possible 16 amino acid linear peptides of the constant region of the heavy chain of IgG1 (Uniprot P01857) were tiled in an overlapping manner. IgA, IgM, and IgG binding to each peptide was quantified for each subject and the fold difference in COVID-19 convalescent/naïve control subjects was plotted for each peptide according to its position in IgG1. Several peptides had increased IgM and IgG binding.

Given the development of RFs in some individuals with infection, we evaluated RFs in COVID-19. RFs were quantified in a traditional manner by measuring total Ig binding to the Fc portion of IgG by ELISA using the sera of COVID-19 convalescent subjects collected 5 weeks post-symptom resolution and COVID-19 naïve subjects collected prior to 2019. As shown in FIG. 7A, RF binding was increased in some COVID-19 convalescent subjects. We next evaluated the fine specificities of RFs in COVID-19. Since citrulline-reactivity is highly specific to RA and since COVID-19 subjects do not bind the citrulline- and homocitrulline-containing IgG epitopes that we identified for RFs in RA (FIG. 4), we evaluated only native epitopes for COVID-19 convalescent subjects. To identify linear epitopes of IgG bound by antibodies, sera from 40 COVID-19 convalescent subjects and 20 COVID-19 naïve subjects were subjected to a high density peptide array in which all possible 16 amino acid linear native peptides of the constant region of the heavy chain of IgG1 (Uniprot P01857) were tiled in an overlapping manner. IgA, IgM, and IgG binding to each peptide was quantified for each subject and the fold difference in COVID-19 convalescent/naïve control subjects was plotted for each peptide according to its position in IgG1. As shown in In FIG. 7B, several peptides had increased IgM or IgG binding. Of particular relevance, the following peptides were identified:

| | |
|---|---|
| P01857-104 | DKTHTCPPCPAPELLG<br>SEQ ID NO: 25 |
| P01857-131 | KDTLMISRTPEVTCW<br>SEQ ID NO: 27 |
| P01857-238 | RDELTKNQVSLTCLVK<br>SEQ ID NO: 28 |
| P01857-293 | LTVDKSRWQQGNVFSC<br>SEQ ID NO: 29 |

Figure 8A:
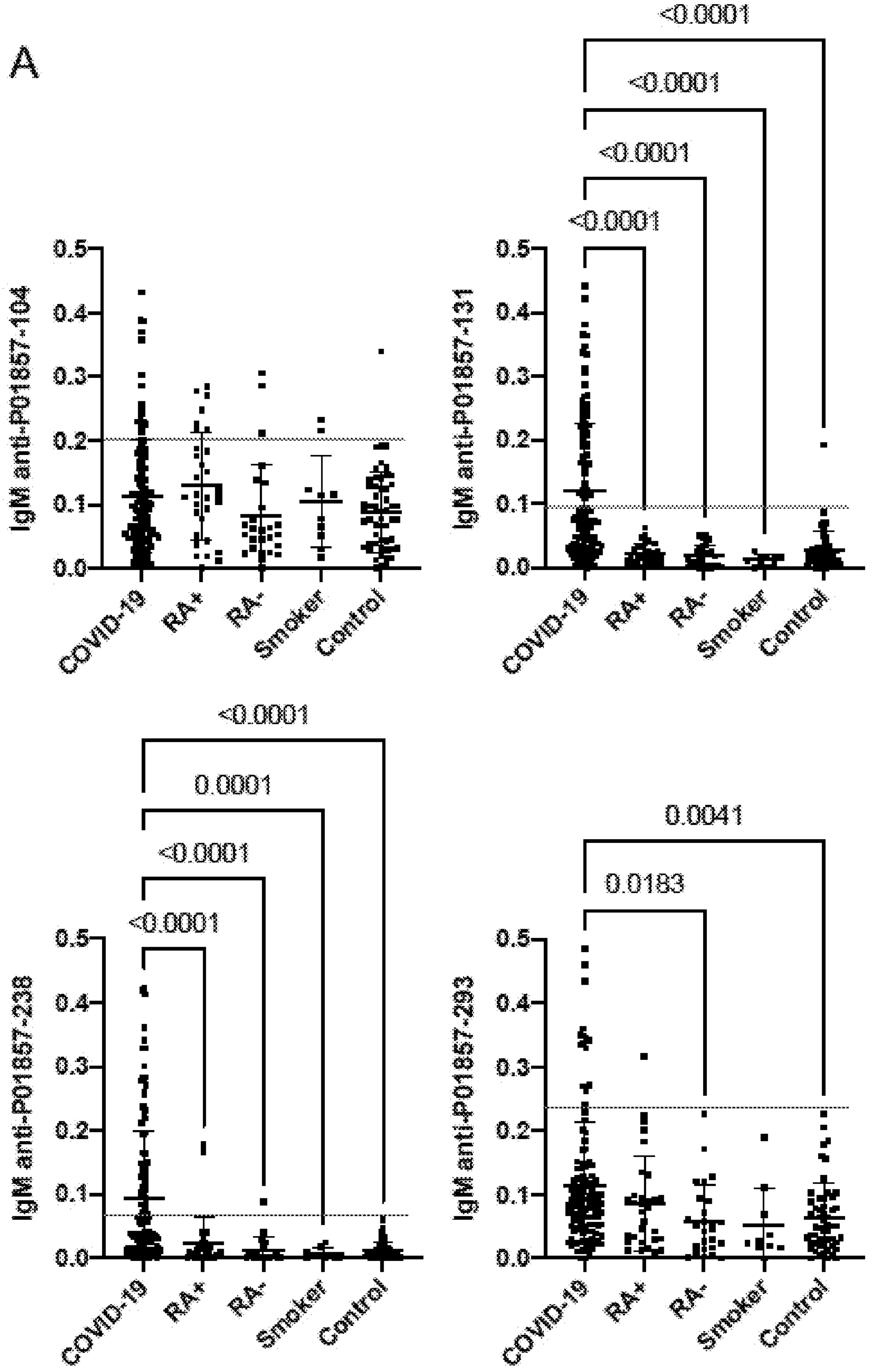
FIGS. 8A and B show increased IgM and IgG binding to IgG1-derived epitopes after COVID-19. Sera from the following subject groups were tested by ELISA for IgM (FIG. 8A) and IgG (FIG. 8B) binding to the IgG1-derived peptides listed on the y axis of each graph (P01857-104, 131, 238, and 293 with the number indicating starting amino acid position of P01857, i.e. IgG1 heavy chain constant region): COVID-19 convalescent subjects 5 weeks post-symptom resolution (n=121), seropositive rheumatoid arthritis subjects (RA+; n=31), seronegative rheumatoid arthritis subjects (RA−; n=26), current smokers (n=10), and non-smoking COVID-19 naïve controls without autoimmune disease collected prior to 2019 (n=54). All groups were compared by Kruskal-Wallis Test with Dunn's Multiple Comparison's Test and p<0.05 was considered significant. As shown in the figure, IgM that binds to P01857-131, 238, and 293 and IgG that binds to P01857-293 are increased in COVID-19 convalescent subjects. Line indicates a possible cut-off for positive testing.
Figure 8B:
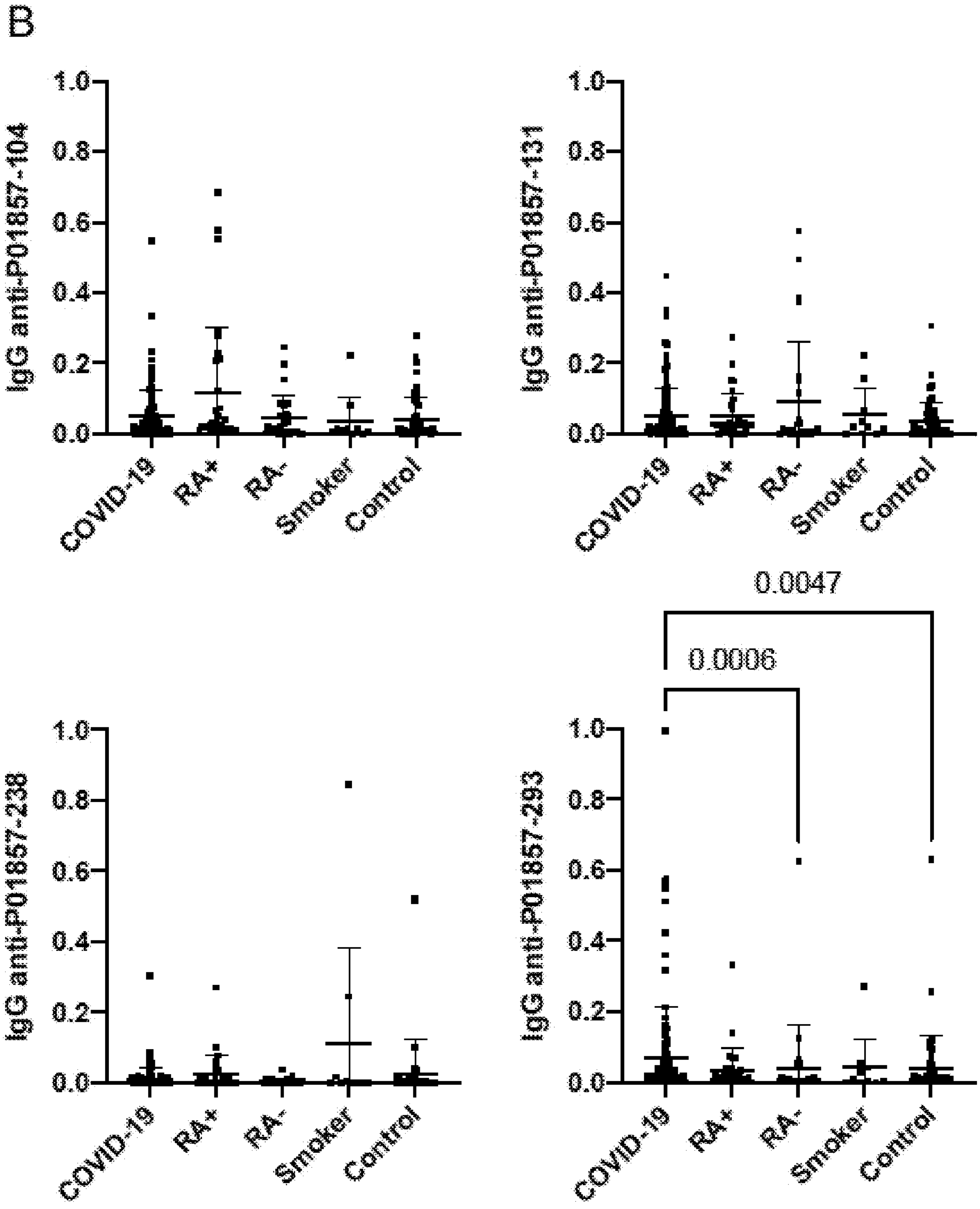

We then further evaluated those four peptides in a larger sample set. Sera from the following subject groups were tested by ELISA for IgM (FIG. 8A) and IgG (FIG. 8B) binding to the IgG1-derived peptides starting at amino acid positions 104, 131, 238, and 293: COVID-19 convalescent subjects 5 weeks post-symptom resolution, seropositive rheumatoid arthritis subjects, seronegative rheumatoid arthritis subjects, current smokers, and non-smoking COVID-19 naïve controls without autoimmune disease. As shown in FIG. 8, IgM that binds to P01857-131 (SEQ ID NO: 27) and P01857-238 (SEQ ID NO: 28) and P01857-293 (SEQ ID NO: 29) and IgG that binds to P01857-293 (SEQ ID NO: 29) are increased in COVID-19 convalescent subjects. Table 3 shows the percent of subjects in each group that would be considered seropositive for IgM antibodies against each peptide using a preliminary cutoff.

TABLE 3

PERCENT OF SUBJECTS IN EACH GROUP THAT WOULD BE CONSIDERED SEROPOSITIVE FOR IGM ANTIBODIES AGAINST EACH PEPTIDE USING A PRELIMINARY CUTOFF

| Peptide | COVID-19 | RA+ | RA− | Smoker | Control |
|---|---|---|---|---|---|
| IgM anti-P01857-104 | 14% | 23% | 12% | 20% | 2% |
| IgM anti-P01857-131 | 45% | 0% | 0% | 0% | 2% |
| IgM anti-P01857-238 | 44% | 6% | 4% | 0% | 0% |
| IgM anti-P01857-293 | 12% | 3% | 0% | 0% | 0% |

Figure 9A:
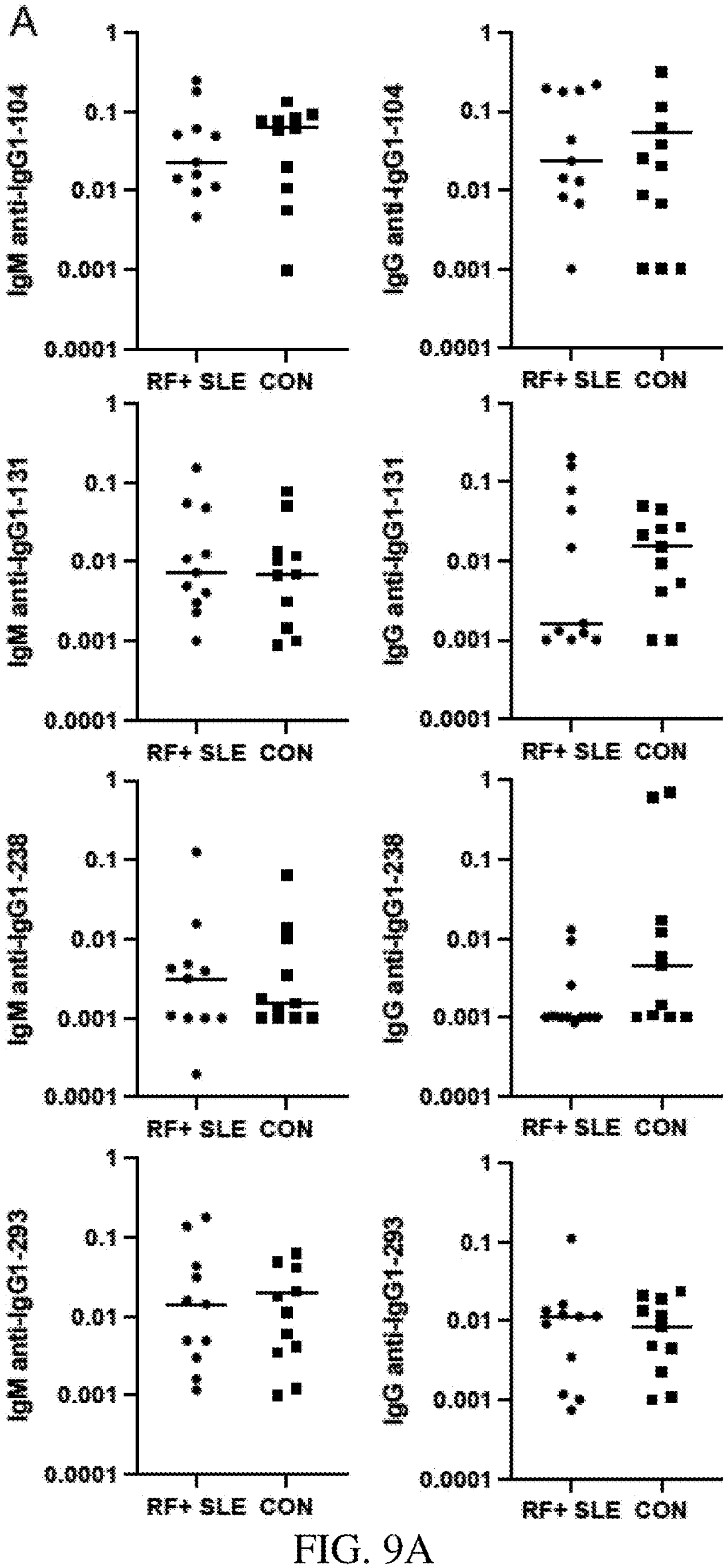
FIGS. 9A and B show that the COVID RFs are not present in Sjogren's disease or lupus (SLE) apart from one RF in Sjogren's disease that binds to a hinge peptide. Sera from subjects with lupus (n=11, FIG. 9A) or Sjogren's disease (SjD, n=15, FIG. 9B) who tested positive for RFs in the past and age- and sex-matched nonautoimmune controls were subjected to ELISA to detect IgM (left column of graphs) and IgG (right column of graphs) binding to peptides starting at positions 104, 131, 238, and 293 of IgG1 (P01857). Lupus and SjD groups were compared to controls by Mann-Whitney test.
Figure 9B:
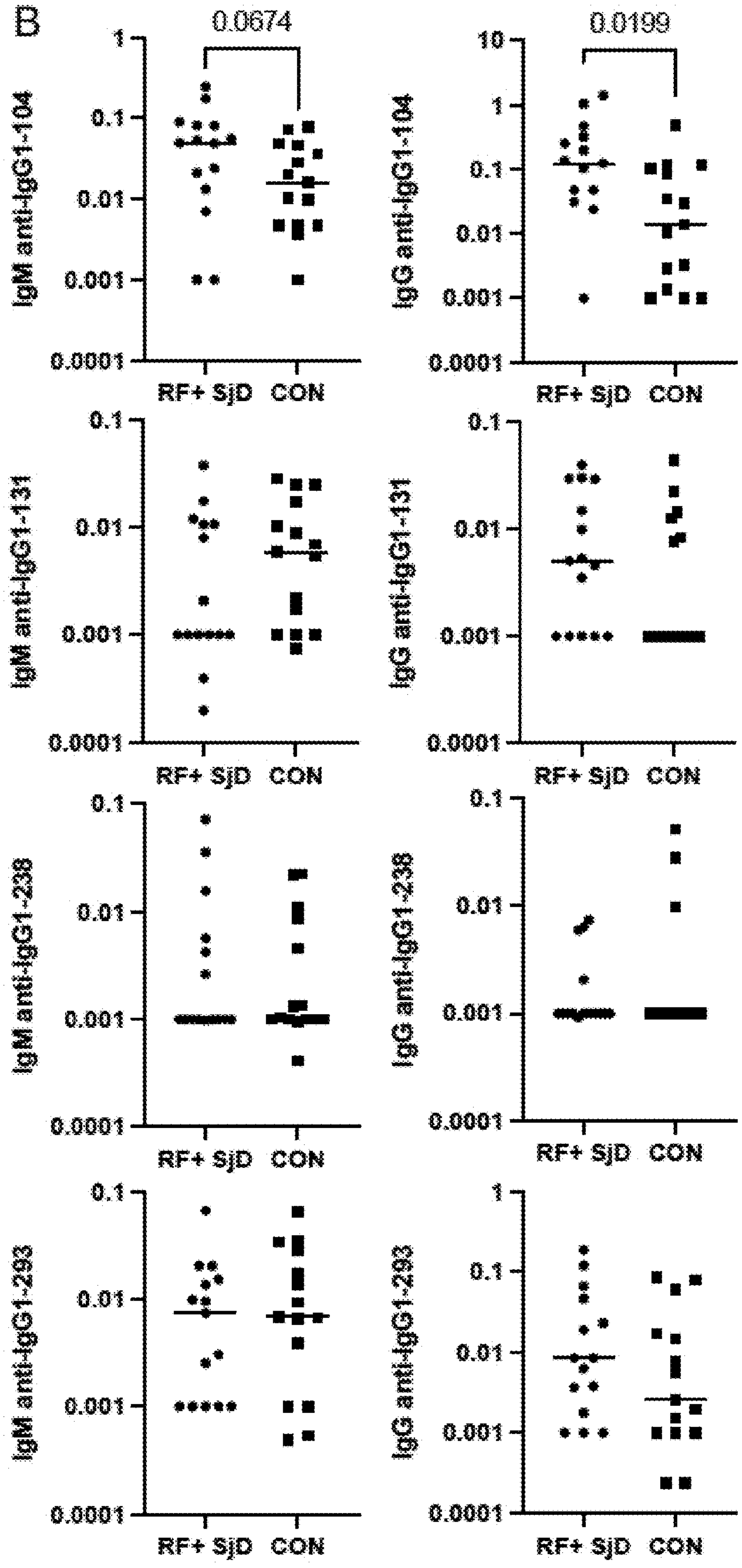

Next, we evaluated if the specific RFs found in COVID-19 could be found in lupus or Sjogren's disease, two autoimmune diseases that commonly elevate RFs. We quantified IgM and IgG binding to these peptides by ELISA using serum from lupus and Sjogren's disease subjects previously found to test positive for RFs by clinical testing. As shown in FIG. 9A, the 4 peptides bound by RFs in COVID-19 are not bound by IgG or IgM in lupus. As shown in FIG. 9B, peptides P01857-131, 238, and 293 are also not bound in Sjogren's disease by IgG or IgM, but P01857-104 is bound by both IgM and IgG in Sjogren's disease, similar to the related hinge peptide P01857-109 (FIG. 3).

Discussion of IgG Epitopes Bound in Covid-19

Together these data demonstrate that there are unique IgG1 epitopes (SEQ ID NO: 27, 28, and 29) bound in COVID-19 that are not bound in RA, Sjogren's Disease, lupus, or smokers. Such peptides can be used together with peptides bound by RFs in RA and Sjogren's disease to create a panel of peptides that can differentiate between RA and other diseases.

Example 3: Pre-Clinical RA

Years and even decades prior to the development of rheumatoid arthritis, anti-CCP and RF autoantibodies develop. Clinical trials are being performed to determine if immune suppressants can prevent RA in these people. However, given the huge variation in time from detecting a positive anti-CCP test to clinically apparent RA (from months to decades), it has been impossible to identify effective strategies to prevent RA. A diagnostic test that can differentiate between anti-CCP+ individuals likely to develop RA imminently from anti-CCP+ individuals not likely to develop RA imminently would enable trials to identify strategies to prevent RA and also identify individuals who would most benefit from preventative treatment.

Figures 10A, 10B:
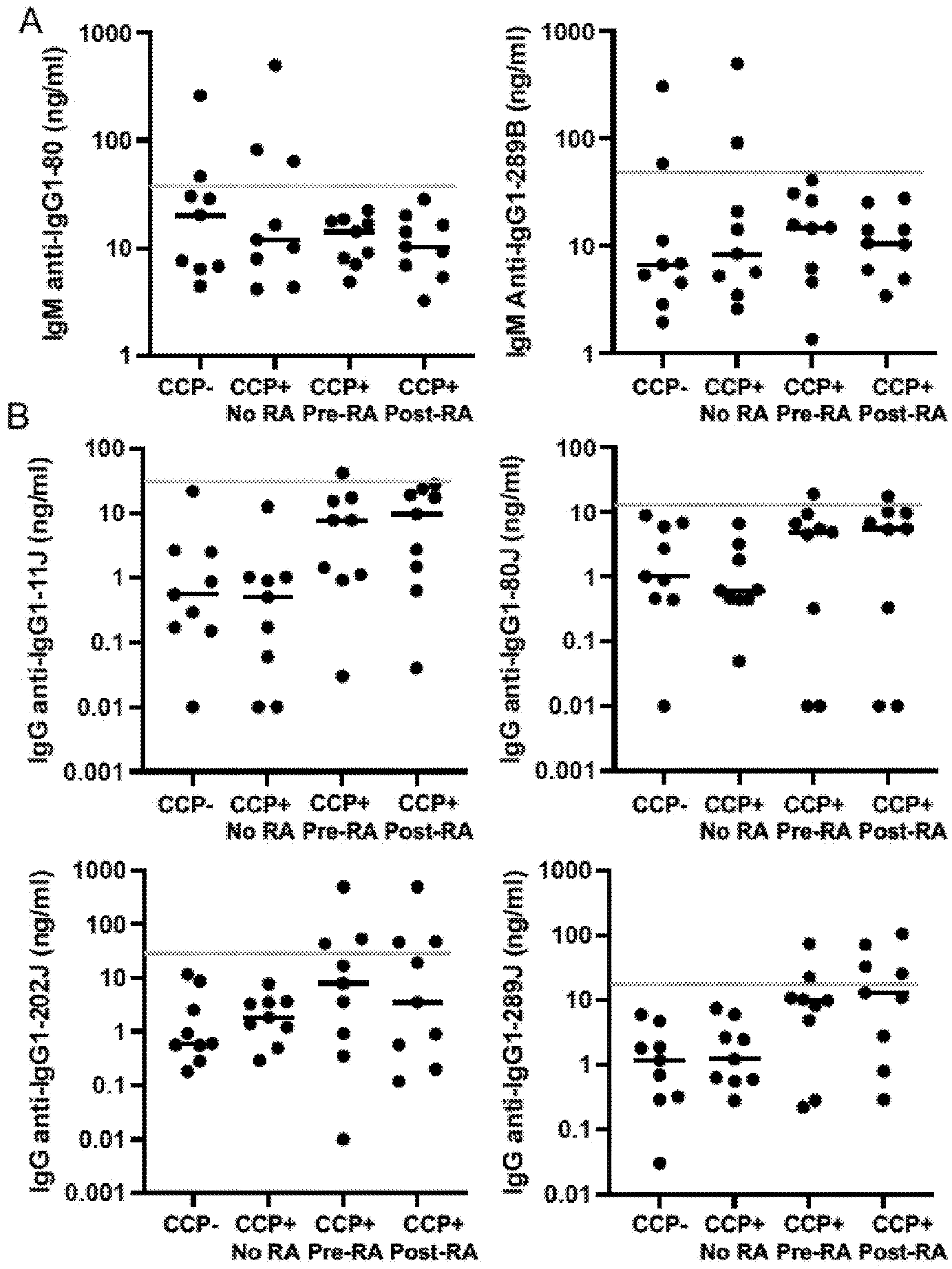
FIGS. 10A and B show that IgG1 peptides can differentiate between anti-CCP+ subjects who develop RA and who do not develop RA in the future. Plasma from anti-CCP− subjects without RA, anti-CCP+ subjects who did not develop RA on average 1447 days after providing plasma (range 300-2920 days), and anti-CCP+ subjects who later developed RA (Pre-RA sample on average 286 days [range 65-400 days] prior to RA development; Post-RA sample after RA development) was subjected to ELISA to detect IgA, IgM, and IgG that bind to native, citrulline (B)-containing, homocitrulline (J)-containing, and dually modified (BJ) versions of IgG1 peptides starting at positions 11, 80, 131, 167, 202, 219, 238, 289, and 293. Examples of peptides with differences between anti-CCP+ No RA subjects and anti-CCP+ Pre-RA subjects are shown. For all panels: bars indicate medians; gray lines indicate potential cutoffs; n=9.

To this end, we evaluated IgA, IgG, and IgM binding to native, citrulline-containing, homocitrulline-containing, and dually modified versions of IgG1 peptides starting at positions 11, 80, 167, 202, 219, and 289, and native versions of 131, 238, and 293 using plasma collected from anti-CCP− subjects without RA, anti-CCP+ subjects who did not develop RA on average 1447 days after providing plasma (range 300-2920 days), and anti-CCP+ subjects who later developed RA on average 286 days (range 65-400 days) after plasma collection. As shown in FIG. 10A, we found that IgM that binds to specific IgG1 peptides (SEQ ID NO: 4 and 21) is higher in CCP− controls and anti-CCP+ subjects who do not develop RA imminently as compared to anti-CCP+ subjects who do develop RA imminently (samples both pre- and post-RA development). Further, anti-CCP+ subjects who later develop RA have higher levels of IgG that binds to specific IgG1 peptides (SEQ ID NO: 2, 5, 13, and 22) compared to anti-CCP− subjects and CCP+ subjects who do not develop RA (FIG. 10B).

Together these data suggest that specific IgG1 peptides can differentiate between CCP+ subjects who do and do not develop RA in the near future (FIG. 10). These peptides could be used in diagnostic tests to identify methods to prevent RA and then later to identify individuals in need of those treatments.

The use of the terms “a” and “an” and “the” and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms “comprising”, “having”, “including”, and “containing” are to be construed as open-ended terms (i.e., meaning “including, but not limited to”) unless otherwise noted. “About” or “approximately” as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, “about” can mean within one or more standard deviations, or within ±10% or 5% of the stated value. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., “such as”), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A citrullinated or homocitrullinated peptide comprising SEQ ID NO. 24, wherein X at position is K or homocitrulline, X at position 9 is K or homocitrulline, and X at position 11 is R or citrulline, or a variant with 1-2 variant amino acids at positions other than positions 4, 9 and 11; wherein the variant peptide detects bound anti-citrullinated or anti-homocitrullinated protein IgA, IgM, IgG1-4, IgE antibodies, or a combination thereof, in an ELISA assay; wherein the peptide is conjugated to a ligand, a detectable label, or a combination thereof; and wherein the peptide includes at least one of a homocitrulline at position 4, a homocitrulline at position 9, or a citrulline at position 11.

2. The peptide of claim 1, wherein the peptide is any of SEQ ID NOs. 21-23.

3. The peptide of claim 1, wherein the peptide does not comprise a full-length IgG constant region.

4. The peptide of claim 1, wherein the ligand comprises biotin, avidin, streptavidin, polymeric streptavidin, neutravidin, a carrier protein, or a lipid.

5. The peptide of claim 1, wherein the detectable label comprises a radioisotope, a fluorescent agent, a chemiluminescent agent, or an enzymatic label.

6. A substrate or device comprising the peptide of claim 1.

7. A method of testing a body fluid or tissue sample from a subject, comprising contacting the sample with the peptide of claim 1, and detecting complexes of the peptide and antibodies in the body fluid or tissue sample.

8. A method of detecting rheumatoid factor in a blood sample from a subject, comprising contacting the blood sample with the peptide of claim 1, and detecting complexes of the peptide and antibodies in the blood sample.

9. The method of claim 7, wherein detecting comprises binding to a peptide array, flow cytometry, an ELISA assay, a multiplex assay, an immunofluorescence assay, or a lateral flow immunoassay.

10. A method of treating a subject, comprising contacting a body fluid or tissue sample from the subject with the peptide of claim 1, detecting complexes of the peptide and antibodies in the body fluid or tissue sample, and, upon detection of complexes, administering to the subject a pre rheumatoid arthritis treatment.

11. The method of claim 10, wherein the subject has a rheumatoid arthritis risk factor selected from a parent or sibling with rheumatoid arthritis, arthralgia but not arthritis, testing positive for anti-citrullinated protein antibodies, having a variant in the human leukocyte antigen (HLA) system, having a previous bacterial or viral infection or colonized with a pathogen such as Epstein-Barr virus, cytomegalovirus, *P. gingivalis, A. actinomycetemcomitans*, or *Prevotella* species, is a smoker, is obese, is a male over 50 years of age, or is a female over 30 years of age.

12. The method of claim 10, wherein the pre rheumatoid arthritis treatment comprises administration of a disease-modifying anti-rheumatic drug (DMARD), a glucocorticoid, vitamin D, omega-3 fatty acid, or a combination thereof.

13. L The method of claim 7, further comprising detecting anti-modified protein antibodies including anti-citrullinated or anti-homocitrullinated protein antibodies in the blood sample.

* * * * *

```
                              SEQUENCE LISTING


Sequence total quantity: 29
SEQ ID NO: 1              moltype = AA  length = 17
FEATURE                   Location/Qualifiers
source                    1..17
                          mol_type = protein
                          note = IgG epitope
                          organism = Synthetic construct
SEQUENCE: 1
LAPSSKSTSG GTAALGC                                                     17

SEQ ID NO: 2              moltype = AA  length = 17
FEATURE                   Location/Qualifiers
source                    1..17
                          mol_type = protein
                          note = IgG epitope
                          organism = Synthetic construct
SEQUENCE: 2
LAPSSJSTSG GTAALGC                                                     17

SEQ ID NO: 3              moltype = AA  length = 17
FEATURE                   Location/Qualifiers
source                    1..17
                          mol_type = protein
                          note = IgG epitope
                          organism = Synthetic construct
```

```
VARIANT                 6
                        note = X can be K or homocitrulline
SEQUENCE: 3
LAPSSXSTSG GTAALGC                                                   17

SEQ ID NO: 4            moltype = AA  length = 24
FEATURE                 Location/Qualifiers
source                  1..24
                        mol_type = protein
                        note = IgG epitope
                        organism = Synthetic construct
SEQUENCE: 4
TYICNVNHKP SNTKVDKKVE PKSC                                           24

SEQ ID NO: 5            moltype = AA  length = 24
FEATURE                 Location/Qualifiers
source                  1..24
                        mol_type = protein
                        note = IgG epitope
                        organism = Synthetic construct
SEQUENCE: 5
TYICNVNHJP SNTJVDJJVE PJSC                                           24

SEQ ID NO: 6            moltype = AA  length = 24
FEATURE                 Location/Qualifiers
source                  1..24
                        mol_type = protein
                        note = IgG epitope
                        organism = Synthetic construct
VARIANT                 14
                        note = X can be K or homocitrulline
VARIANT                 17
                        note = X can be K or homocitrulline
VARIANT                 18
                        note = X can be K or homocitrulline
VARIANT                 22
                        note = X can be K or homocitrulline
VARIANT                 9
                        note = X can be K or homocitrulline
SEQUENCE: 6
TYICNVNHXP SNTXVDXXVE PXSC                                           24

SEQ ID NO: 7            moltype = AA  length = 22
FEATURE                 Location/Qualifiers
source                  1..22
                        mol_type = protein
                        note = IgG epitope
                        organism = Synthetic construct
SEQUENCE: 7
VHNAKTKPRE EQYNSTYRVV SV                                             22

SEQ ID NO: 8            moltype = AA  length = 22
FEATURE                 Location/Qualifiers
source                  1..22
                        mol_type = protein
                        note = IgG epitope
                        organism = Synthetic construct
SEQUENCE: 8
VHNAKTKPBE EQYNSTYBVV SV                                             22

SEQ ID NO: 9            moltype = AA  length = 22
FEATURE                 Location/Qualifiers
source                  1..22
                        mol_type = protein
                        note = IgG epitope
                        organism = Synthetic construct
SEQUENCE: 9
VHNAJTJPRE EQYNSTYRVV SV                                             22

SEQ ID NO: 10           moltype = AA  length = 22
FEATURE                 Location/Qualifiers
source                  1..22
                        mol_type = protein
                        note = IgG epitope
                        organism = Synthetic construct
SEQUENCE: 10
VHNAJTJPBE EQYNSTYBVV SV                                             22

SEQ ID NO: 11           moltype = AA  length = 22
```

-continued

```
FEATURE                 Location/Qualifiers
source                  1..22
                        mol_type = protein
                        note = IgG epitope
                        organism = Synthetic construct
VARIANT                 5
                        note = X can be K or homocitrulline
VARIANT                 7
                        note = X can be K or homocitrulline
VARIANT                 9
                        note = X can be R or citrulline
VARIANT                 18
                        note = X can be R or citrulline
SEQUENCE: 11
VHNAXTXPXE EQYNSTYXVV SV                                            22

SEQ ID NO: 12           moltype = AA  length = 13
FEATURE                 Location/Qualifiers
source                  1..13
                        mol_type = protein
                        note = IgG epitope
                        organism = Synthetic construct
SEQUENCE: 12
YKCKVSNKAL PAP                                                      13

SEQ ID NO: 13           moltype = AA  length = 13
FEATURE                 Location/Qualifiers
source                  1..13
                        mol_type = protein
                        note = IgG epitope
                        organism = Synthetic construct
SEQUENCE: 13
YJCJVSNJAL PAP                                                      13

SEQ ID NO: 14           moltype = AA  length = 13
FEATURE                 Location/Qualifiers
source                  1..13
                        mol_type = protein
                        note = IgG epitope
                        organism = Synthetic construct
VARIANT                 2
                        note = X can be K or homocitrulline
VARIANT                 4
                        note = X can be K or homocitrulline
VARIANT                 8
                        note = X can be K or homocitrulline
SEQUENCE: 14
YXCXVSNXAL PAP                                                      13

SEQ ID NO: 15           moltype = AA  length = 23
FEATURE                 Location/Qualifiers
source                  1..23
                        mol_type = protein
                        note = IgG epitope
                        organism = Synthetic construct
SEQUENCE: 15
ISKAKGQPRE PQVYTLPPSR DEL                                           23

SEQ ID NO: 16           moltype = AA  length = 23
FEATURE                 Location/Qualifiers
source                  1..23
                        mol_type = protein
                        note = IgG epitope
                        organism = Synthetic construct
SEQUENCE: 16
ISJAJGQPRE PQVYTLPPSR DEL                                           23

SEQ ID NO: 17           moltype = AA  length = 23
FEATURE                 Location/Qualifiers
source                  1..23
                        mol_type = protein
                        note = IgG eiptope
                        organism = Synthetic construct
SEQUENCE: 17
ISKAKGQPBE PQVYTLPPSB DEL                                           23

SEQ ID NO: 18           moltype = AA  length = 23
FEATURE                 Location/Qualifiers
source                  1..23
```

```
                         mol_type = protein
                         note = IgG epitope
                         organism = Synthetic construct
SEQUENCE: 18
ISJAJGQPBE PQVYTLPPSB DEL                                           23

SEQ ID NO: 19            moltype = AA  length = 23
FEATURE                  Location/Qualifiers
source                   1..23
                         mol_type = protein
                         note = IgG epitope
                         organism = Synthetic construct
VARIANT                  3
                         note = X can be K or homocitrulline
VARIANT                  5
                         note = X can be K or homocitrulline
VARIANT                  9
                         note = X can be R or citrulline
VARIANT                  20
                         note = X can be R or citrulline
SEQUENCE: 19
ISXAXGQPXE PQVYTLPPSX DEL                                           23

SEQ ID NO: 20            moltype = AA  length = 19
FEATURE                  Location/Qualifiers
source                   1..19
                         mol_type = protein
                         note = IgG epitope
                         organism = Synthetic construct
SEQUENCE: 20
LYSKLTVDKS RWQQGNVFS                                                19

SEQ ID NO: 21            moltype = AA  length = 19
FEATURE                  Location/Qualifiers
source                   1..19
                         mol_type = protein
                         note = IgG epitope
                         organism = Synthetic construct
SEQUENCE: 21
LYSKLTVDKS BWQQGNVFS                                                19

SEQ ID NO: 22            moltype = AA  length = 19
FEATURE                  Location/Qualifiers
source                   1..19
                         mol_type = protein
                         note = IgG epitope
                         organism = Synthetic construct
SEQUENCE: 22
LYSJLTVDJS RWQQGNVFS                                                19

SEQ ID NO: 23            moltype = AA  length = 19
FEATURE                  Location/Qualifiers
source                   1..19
                         mol_type = protein
                         note = IgG epitope
                         organism = Synthetic construct
SEQUENCE: 23
LYSJLTVDJS BWQQGNVFS                                                19

SEQ ID NO: 24            moltype = AA  length = 19
FEATURE                  Location/Qualifiers
source                   1..19
                         mol_type = protein
                         note = IgG epitope
                         organism = Synthetic construct
VARIANT                  4
                         note = X can be K or homocitrulline
VARIANT                  9
                         note = X can be K or homocitrulline
VARIANT                  11
                         note = X can be R or citrulline
SEQUENCE: 24
LYSXLTVDXS XWQQGNVFS                                                19

SEQ ID NO: 25            moltype = AA  length = 16
FEATURE                  Location/Qualifiers
source                   1..16
                         mol_type = protein
                         note = IgG epitope
```

-continued

```
                        organism = Synthetic construct
SEQUENCE: 25
DKTHTCPPCP APELLG                                                       16

SEQ ID NO: 26           moltype = AA  length = 15
FEATURE                 Location/Qualifiers
source                  1..15
                        mol_type = protein
                        note = IgG epitope
                        organism = Synthetic construct
SEQUENCE: 26
CPPCPAPELL GGPSV                                                        15

SEQ ID NO: 27           moltype = AA  length = 16
FEATURE                 Location/Qualifiers
source                  1..16
                        mol_type = protein
                        note = IgG epitope
                        organism = Synthetic construct
SEQUENCE: 27
KDTLMISRTP EVTCVV                                                       16

SEQ ID NO: 28           moltype = AA  length = 16
FEATURE                 Location/Qualifiers
source                  1..16
                        mol_type = protein
                        note = IgG epitope
                        organism = Synthetic construct
SEQUENCE: 28
RDELTKNQVS LTCLVK                                                       16

SEQ ID NO: 29           moltype = AA  length = 16
FEATURE                 Location/Qualifiers
source                  1..16
                        mol_type = protein
                        note = IgG epitope
                        organism = Synthetic construct
SEQUENCE: 29
LTVDKSRWQQ GNVFSC                                                       16
```